(12) United States Patent
Yamamoto et al.

(10) Patent No.: US 10,869,937 B2
(45) Date of Patent: Dec. 22, 2020

(54) POLYMER DERIVATIVES, AND NOVEL POLYMER DERIVATIVE IMAGING PROBE USING SAME

(71) Applicant: Nippon Kayaku Kabushiki Kaisha, Tokyo (JP)

(72) Inventors: Keiichirou Yamamoto, Tokyo (JP); Yuki Kawano, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/319,636

(22) PCT Filed: Jul. 21, 2017

(86) PCT No.: PCT/JP2017/026408
§ 371 (c)(1),
(2) Date: Jan. 22, 2019

(87) PCT Pub. No.: WO2018/025657
PCT Pub. Date: Feb. 8, 2018

(65) Prior Publication Data
US 2019/0307905 A1    Oct. 10, 2019

(30) Foreign Application Priority Data
Jul. 30, 2016 (JP) ................. 2016-150886

(51) Int. Cl.
| | | |
|---|---|---|
| *A61K 49/00* | (2006.01) |
| *C08G 65/333* | (2006.01) |
| *C08G 69/40* | (2006.01) |
| *A61K 47/34* | (2017.01) |
| *A61K 9/51* | (2006.01) |

(52) U.S. Cl.
CPC ............ *A61K 49/0054* (2013.01); *A61K 9/51* (2013.01); *A61K 47/34* (2013.01); *A61K 49/00* (2013.01); *C08G 65/33396* (2013.01); *C08G 69/40* (2013.01)

(58) Field of Classification Search
CPC ............................ A61K 49/0054; A61K 47/34
See application file for complete search history.

(56) References Cited

U.S. PATENT DOCUMENTS

| | | | |
|---|---|---|---|
| 5,593,658 A | 1/1997 | Bogdanov et al. |
| 2006/0067910 A1 | 3/2006 | Kitagawa et al. |
| 2006/0099265 A1 | 5/2006 | Shimizu et al. |
| 2008/0019908 A1 | 1/2008 | Akitsu et al. |
| 2008/0113028 A1 | 5/2008 | Shimizu et al. |
| 2009/0156742 A1 | 6/2009 | Shimizu et al. |
| 2009/0239782 A1 | 9/2009 | Nakamura et al. |
| 2010/0234537 A1 | 9/2010 | Kitagawa et al. |
| 2010/0292414 A1 | 11/2010 | Kitagawa et al. |
| 2012/0149649 A1 | 6/2012 | Kato et al. |
| 2012/0321583 A1 | 12/2012 | Yurkovetskiy et al. |
| 2013/0122103 A1 | 5/2013 | Kishimura et al. |
| 2013/0149252 A1 | 6/2013 | Hara et al. |
| 2013/0280306 A1 | 10/2013 | Sill et al. |
| 2014/0024703 A1 | 1/2014 | Shimizu et al. |
| 2014/0142167 A1 | 5/2014 | Shimizu et al. |
| 2014/0155577 A1* | 6/2014 | Parquette ............... A61K 47/62 530/330 |
| 2015/0011715 A1 | 1/2015 | Nakamura et al. |
| 2015/0064265 A1 | 3/2015 | Fahmy et al. |
| 2015/0087788 A1 | 3/2015 | Docon et al. |
| 2015/0258219 A1 | 9/2015 | Kataoka et al. |
| 2015/0259479 A1 | 9/2015 | Shimizu et al. |

(Continued)

FOREIGN PATENT DOCUMENTS

| | | |
|---|---|---|
| CN | 103131005 A | 6/2013 |
| CN | 105267991 A | 1/2016 |

(Continued)

OTHER PUBLICATIONS

International Search Report and Written Opinion dated Sep. 5, 2017 in corresponding PCT application No. PCT/JP2017/026408.

(Continued)

*Primary Examiner* — Mark S Kaucher
(74) *Attorney, Agent, or Firm* — Nields, Lemack & Frame, LLC

(57) ABSTRACT

Provided are a block copolymer having an enhanced effect of imaging the interior of a tumor compared to known block copolymers and imaging probes using the known block copolymers; and an imaging probe using the block copolymer. Specifically, for the purpose of enhancing penetrability into a diseased target tissue and efficiently enhancing an imaging effect compared to known block copolymers and imaging probes using the known block copolymers, disclosed is a block copolymer in which a hydrophilic polymer segment containing a polyethylene glycol chain is linked to a hydrophobic polymer segment containing a polyamino acid chain having a signal group and optionally a hydrophobic substituent in a side chain, wherein the main chain polymer combining the polyethylene glycol chain and the polyamino acid chain has an average molecular weight of not less than 2 kDa and not more than 10 kDa, and the mass content percentage of the signal group and the optional hydrophobic substituent is not less than 5% by mass and not more than 50% by mass; and also disclosed is a composition including the block copolymer.

3 Claims, 5 Drawing Sheets

(56) References Cited

U.S. PATENT DOCUMENTS

| | | | | |
|---|---|---|---|---|
| 2015/0290185 | A1* | 10/2015 | Yamamoto | A61K 31/4184 525/450 |
| 2016/0279164 | A1 | 9/2016 | Nakamura et al. | |
| 2016/0287714 | A1 | 10/2016 | Kataoka et al. | |

FOREIGN PATENT DOCUMENTS

| | | |
|---|---|---|
| JP | 5-117385 A | 5/1993 |
| JP | 6-206832 A | 7/1994 |
| JP | 4528990 B2 | 8/2010 |
| JP | 2011-173802 A | 9/2011 |
| JP | 4936312 B2 | 5/2012 |
| JP | 5714016 B2 | 5/2015 |
| TW | 201427693 A | 7/2014 |
| TW | 201613652 A | 4/2016 |
| WO | 1994/005203 A1 | 3/1994 |
| WO | 2004/039869 A1 | 5/2004 |
| WO | 2004/082718 A1 | 9/2004 |
| WO | 2006/033296 A1 | 3/2006 |
| WO | 2007/111211 A1 | 10/2007 |
| WO | 2008/041610 A1 | 4/2008 |
| WO | 2009/041570 A1 | 4/2009 |
| WO | 2012/014942 A1 | 2/2012 |
| WO | 2013/154774 A1 | 10/2013 |
| WO | 2013/155487 A1 | 10/2013 |
| WO | 2014/058079 A1 | 4/2014 |
| WO | 2014/073447 A1 | 5/2014 |
| WO | 2014/093394 A1 | 6/2014 |
| WO | 2015/075942 A1 | 5/2015 |
| WO | 2015/125640 A1 | 8/2015 |
| WO | 2016/103867 A1 | 6/2016 |

OTHER PUBLICATIONS

Anraku et al., "Spontaneous Formation of Nanosized Unilamellar Polyion Complex Vesicles with Tunable Size and Properties", Journal of American Chemical Society, 2010, vol. 132, p. 1631-1636.

Cabral et al., "Systemic Targeting of Lymph Node Metastasis through the Blood Vascular System by Using Size-Controlled Nanocarriers", ACS Nano, (2015) vol. 9(5), p. 4957-4967.

Matsumura, "Poly (amino acid) micelle nanocarriers in preclinical and clinical studies", Advanced Drug Delivery Reviews, (2008) vol. 60, p. 899-914.

Prabhakar et al., "Challenges and Key Considerations of the Enhanced Permeability and Retention Effect for Nanomedicine Drug Delivery in Oncology", Cancer Research, (2013) vol. 73, p. 2412-2417.

European communication dated Mar. 10, 2020 in corresponding European patent application No. 17836763.7.

Kumagai et al., "Iron Hydroxide Nanoparticles Coated with Poly(Ethylene Glycol)-Poly(Aspartic Acid) Block Copolymer as Novel Magnetic Resonance Contrast Agents for in vivo Cancer Imaging", Colloids and Surfaces B: Biointerfaces, vol. 56, pp. 174-181, 2007.

Zhao et al., "Enhanced Cellular Uptake and Phototoxicity of Verteporfin-Conjugated Gold Nanoparticles as Theranostic Nanocarriers for Targeted Photodynamic Therapy and Imaging of Cancers", Materials Science and Engineering C, vol. 67, pp. 611-622, 2016.

Chinese communication, with English translation, dated Sep. 27, 2020 in corresponding Chinese patent application No. 201780045619.6.

* cited by examiner

POLYMER DERIVATIVES, AND NOVEL POLYMER DERIVATIVE IMAGING PROBE USING SAME

TECHNICAL FIELD

The present invention relates to novel polymer derivatives and a novel polymer derivative imaging probe using those polymer derivatives.

RELATED ART

Development of drug delivery systems (DDS) that control the pharmacokinetics of a physiologically active substance, which is an active ingredient for a pharmaceutical product, and delivers the physiologically active substance to a specific site of action in vivo in a desired drug concentration-reaction time, is underway. Non Patent Literature 1 discloses a DDS preparation including a block copolymer in which a polyethylene glycol segment is linked to a polyamino acid segment, as a drug transport carrier. This block copolymer forms polymeric micelles shape having a particle size of 20 to 100 nm, each micelle having a polyethylene glycol outer shell and a hydrophobic inner core, and the polymeric micelles stably include various kinds of drugs in the inner core by means of chemical bonding or physical uptake.

This polymeric micelle type DDS preparation is characterized in that the DDS preparation has an EPR (a phenomenon in which particles having a particle size of 100 nm or less specifically collect in the blood vessels near a tumor site or an inflammation site, where permeability is high compared to normal blood vessels) effect; that excretion is suppressed when the DDS preparation is administered into the living body, and in vivo retention characteristics are enhanced; and that the DDS preparation passively migrates to and accumulates in tissues such as tumors. Based on these properties, a polymeric micelle type DDS preparation may keep a physiologically active substance in the living body for a long time and may thus increase the rate of utilization of the active ingredient. That is, a polymeric micelle type DDS preparation brings a more powerful physiological activity effect compared to the drug mounted therein.

Patent Literature 1 and Patent Literature 2 disclose polymeric micelle type DDS preparations, in which paclitaxel is physically incorporated. Patent Literature 3 describes a polymeric micelle type DDS preparation to which a camptothecin derivative is chemically bonded, and Patent Literature 4 describes a polymeric micelle type DDS preparation to which a resorcinol derivative is chemically bonded. Patent Literature 5 describes a polymeric micelle type DDS preparation to which a taxane derivative is chemically bonded, and Patent Literature 6 describes a polymeric micelle type DDS preparation to which a steroid derivative is chemically bonded. Various drugs may be applied to polymeric micelle type DDS preparations, and various block copolymers and polymeric micelle type DDS preparations are known.

Furthermore, Patent Literature 7 discloses a novel functional material for the detection of substances in a biological sample or in vivo imaging, the material utilizing the characteristics inherent to nanosized liposomes. Patent Literature 8 and Patent Literature 9 disclose nanoparticles of amphiphilic block copolymers, each block copolymer including a hydrophilic block formed from polysarcosine and a hydrophobic block formed from polylactic acid. It is described that tumor tissues may be subjected to fluorescence imaging by the EPR effect.

Meanwhile, it is contemplated in Non Patent Literature 2 that since the EPR effect varies depending on the tumor type and the animal type, this variance may possibly affect the in vivo behavior of the polymeric micelle type DDS preparation. Non Patent Literature 3 reports that there are animal models with which it is easy to show the EPR effect, and animal models with which it is difficult to show the EPR effect, by using polymeric micelle type DDS preparations having particle sizes of 30 nm and 70 nm, and that a polymeric micelle type DDS preparation having a particle size of 30 nm shows the effects of the DDS preparation even in an animal model with low EPR effect.

Thus, there is a demand for a probe capable of in vivo imaging, which is not affected by the differences in the EPR effect and may be utilized even in cancer tissues.

PRIOR ART LITERATURE

Patent Literature

Patent Literature 1: WO 2004/082718 A
Patent Literature 2: WO 2006/033296 A
Patent Literature 3: WO 2004/039869 A
Patent Literature 4: WO 2008/041610 A
Patent Literature 5: WO 2007/111211 A
Patent Literature 6: WO 2009/041570 A
Patent Literature 7: JP 4528990 B2
Patent Literature 8: JP 4936312 B2
Patent Literature 9: JP 5714016 B2

Non Patent Literature

Non Patent Literature 1: Advanced Drug Delivery Reviews, (2008) Vol. 60, p. 899-914
Non Patent Literature 2: Cancer Research, (2013) Vol. 73, p. 2412-2417
Non Patent Literature 3: ACS Nano, (2015) Vol. 9(5), p. 4957-4967

SUMMARY OF INVENTION

Technical Problem

It is an object of the present invention to provide a block copolymer having an enhanced effect of imaging the interior of a tumor compared to known block copolymers and imaging probes using the known block copolymers, and an imaging probe using the block copolymer. Specifically, it is an object of the invention to enhance the penetrability into a diseased target tissue and to improve an imaging effect, compared to known block copolymers and imaging probes using the known block copolymers.

Solution to Problem

The inventors of the present invention found that a block copolymer having a hydrophilic polymer segment linked to a hydrophobic polymer segment, the hydrophilic polymer segment containing a polyethylene glycol chain, and the hydrophobic polymer segment containing a polyamino acid chain having a signal group and optionally a hydrophobic substituent in a side chain, in which the main chain polymer combining the polyethylene glycol chain and the polyamino acid chain has an average molecular weight of not less than 2 kDa and not more than 10 kDa, and a mass content percentage of the signal group and the optional hydrophobic substituent is not less than 5% by mass and not more than 50% by mass; or a composition including that block copolymer, forms nanoparticles based on associating properties and exhibits kinetics by which penetrability into tumors may be enhanced. Thus, the inventors completed the present invention.

That is, the present invention relates to the following items [1] to [9].

[1] A block copolymer including a hydrophilic polymer segment linked to a hydrophobic polymer segment, the hydrophilic polymer segment containing a polyethylene glycol chain, and the hydrophobic polymer segment containing a polyamino acid chain having a signal group and optionally a hydrophobic substituent in a side chain, wherein the main chain polymer combining the polyethylene glycol chain and the polyamino acid chain has an average molecular weight of not less than 2 kDa and not more than 10 kDa, and a mass content percentage of the signal group and the optional hydrophobic substituent is not less than 5% by mass and not more than 50% by mass.

[2] The block copolymer according to the above-described item [1], wherein the polyamino acid chain is a polyaspartic acid chain, a polyglutamic acid chain, or a poly(aspartic acid-glutamic acid) chain.

[3] The block copolymer according to the above-described item [1] or [2], wherein the hydrophobic substituent is bonded to a side-chain carboxy group by an ester bond and/or an amide bond.

[4] The block copolymer according to any one of the above-described items [1] to [3], wherein the signal group is a fluorescent group.

[5] The block copolymer according to any one of the above-described items [1] to [4], wherein the polyethylene glycol chain has an average molecular weight of not less than 1 kDa and not more than 6 kDa.

[6] The block copolymer according to any one of the above-described items [1] to [5], wherein the block copolymer is represented by General Formula (1):

[Chemical Formula 1]

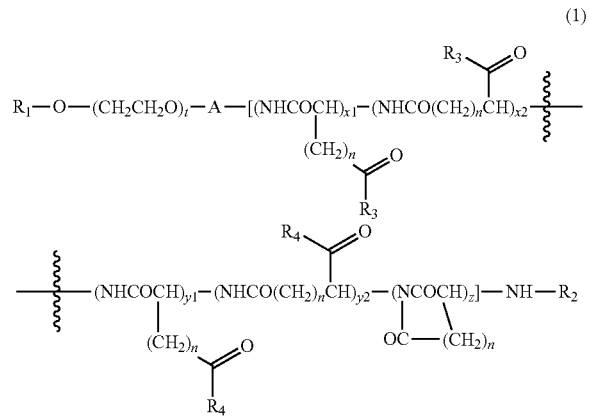

wherein $R_1$ represents a hydrogen atom or a linear, branched or cyclic (C1-C6) alkyl group which may have a substituent; t represents an integer from 20 to 140; A represents a (C1-C6) alkylene group which may have a substituent; $R_2$ represents a substituent selected from the group consisting of a hydrogen atom, a (C1-C6) acyl group, and a (C1-C6) alkoxycarbonyl group; $R_3$ represents a signal group; $R_4$ represents a hydrophobic substituent; n represents 1 or 2; $x_1$, $x_2$, $y_1$, $y_2$, and z each independently represent an integer from 0 to 20; $(x_1+x_2)$ represents an integer from 1 to 10; $(x_1+x_2+y_1+y_2+z)$ represents an integer from 3 to 20; and the various constituent units to which $R_3$ and $R_4$ are bonded, and a constituent unit formed by intramolecular cyclization of a side-chain carbonyl group constitute a structure with those constituent units being each independently randomly arranged.

[7] The block copolymer according to any one of the above-described items [1] to [6], wherein the particles have a particle size of less than 20 nm.

[8] Nanoparticles formed from a composition including the block copolymer according to any one of the above-described items [1] to [7].

[9] The nanoparticles according to the above-described item [8], wherein the nanoparticles have a particle size of less than 20 nm.

[10] An imaging probe including the block copolymer according to any one of the above-described items [1] to [7] and/or the nanoparticles according to the above-described item [8] or [9].

Advantageous Effects of Invention

The present invention relates to a block copolymer having a hydrophilic polymer segment linked to a hydrophobic polymer segment, the hydrophilic polymer segment containing a polyethylene glycol chain, and the hydrophobic polymer segment having a signal group and optionally a substituent in a side chain, wherein the main chain polymer combining the polyethylene glycol chain and the polyamino acid chain has an average molecular weight of not less than 2 kDa and not more than 10 kDa, and the mass content percentage of the signal group and the optional hydrophobic substituent is not less than 5% by mass and not more than 50% by mass; and a composition including that block copolymer.

Nanoparticles formed from the block copolymer of the present invention or a composition including that block copolymer have a volume average particle size that is smaller than that of known polymeric micelle type DDS preparations, and the nanoparticles migrate and penetrate into a target tissue after being administered into the living body. Therefore, the block copolymer of the present invention or a composition including that block copolymer has high migration characteristics and penetrability toward a target tissue compared to known block copolymers, distributes signal groups over a wide range in a diseased target tissue, and efficiently exhibits an imaging effect. Furthermore, the block copolymer of the present invention or a composition including that block copolymer exhibits enhanced excretability in the kidneys and the like and suppressed blood retention characteristics, and thus, the block copolymer or the composition has low distribution in tissues other than the target tissue. Therefore, the imaging effect of the block copolymer of the present invention or a composition including that block copolymer is suppressed in normal tissues.

DETAILED DESCRIPTION OF INVENTION

Figure 1:
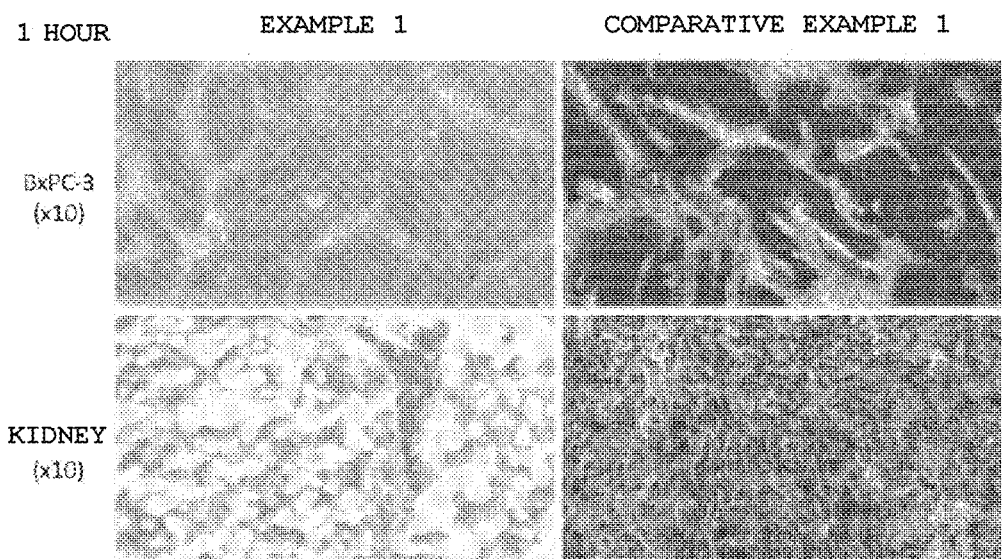
FIG. 1 is a set of tissue section images showing the distributions of the block copolymer of the present invention in a human pancreatic cancer BxPC-3 tumor and in the kidney (Test Example 1).

The present invention relates to a block copolymer having a hydrophilic polymer segment linked to a hydrophobic polymer segment, the hydrophilic polymer segment containing a polyethylene glycol chain, and the hydrophobic polymer segment containing a polyamino acid chain having a signal group and optionally a hydrophobic substituent in a side chain, wherein the main chain polymer combining the polyethylene glycol chain and the polyamino acid chain has an average molecular weight of not less than 2 kDa and not more than 10 kDa, and the mass content percentage of the signal group and the optional hydrophobic substituent is not less than 5% by mass and not more than 50% by mass; and a composition including that block copolymer.

The present invention relates to a block copolymer having a hydrophilic polymer segment containing a polyethylene glycol chain, linked to a hydrophobic polymer segment containing a polyamino acid chain having a substituent in a side chain. The block copolymer of the present invention may be used as a carrier for a signal group, a physiologically active substance, or the like. As long as the block copolymer of the present invention may be able to include a signal group, a physiologically active substance, or the like stably into the inner core by chemical bonding to the block copolymer or by physical incorporation, the block copolymer is not affected by the imaging function or the chemical structure and physical properties of the signal group, or by the pharmacological activity function or the chemical structure and physical properties of the physiologically active substance, and therefore, the block copolymer of the present invention may be utilized as a carrier for all kinds of substances.

The block copolymer of the present invention or a composition including that block copolymer is used as an imaging probe. The details of the block copolymer and the composition will be explained below.

The copolymer including a hydrophilic polymer segment portion containing a polyethylene glycol chain, and a hydrophobic polymer segment containing a polyamino acid chain having a signal group and optionally a hydrophobic substituent in a side chain according to the present invention includes a graft type polymer and a block type polymer. A preferred example of the copolymer is a block type polymer.

The hydrophilic polymer segment containing a polyethylene glycol chain (hereinafter, "polyethylene glycol segment") in the block copolymer of the present invention is a segment having a repeated structure of an ethyleneoxy group: ($CH_2CH_2O$) unit. Preferably, the number of repetitions of the ethyleneoxy group unit is 10 to 180 units, preferably 20 to 140 units, more preferably 22 to 130 units, and even more preferably 30 to 120 units. When the number of repetitions of the ethyleneoxy group unit is 20 or fewer units, the possibility that the block copolymer thus obtainable may not have sufficient water-solubility is increased, and further, there is a possibility that the block copolymer may not exhibit desired disposition. Furthermore, when the number of repetitions is 140 or more units, since the relative content of the hydrophobic polymer segment is lowered, there is a possibility that desired self-associating properties might not be obtained, and the block copolymer may not exhibit the disposition associated with such self-associating properties. Meanwhile, the number of polymerizations of the ethyleneoxy group unit is represented by t in General Formula (1) described below.

In a case in which the number of repetitions of the ethyleneoxy group unit is 10 to 180 units, the molecular weight of the polyethylene glycol segment is 0.4 kDa to 8 kDa; in a case in which the number of repetitions is 20 to 140 units, the molecular weight is 0.8 kDa to 6 kDa; in a case in which the number of repetitions is 22 to 130 units, the molecular weight is 1 kDa to 6 kDa; and in a case in which the number of repetitions is 30 to 120 units, the molecular weight is 1 kDa to 5 kDa.

Regarding the molecular weight of the polyethylene glycol segment used in the present invention, the average molecular weight of the polyethylene glycol segment structural compound used at the time of producing the block copolymer of the invention, which is determined from the peak top molecular weight measured by a GPC method based on polyethylene glycol standards, is employed, and as the calculated value, a value rounded off to the nearest hundred is used.

One terminal group of the polyethylene glycol segment (in General Formula (1) that will be described below, the terminal group corresponds to $R_1$) is not particularly limited, and examples include a hydrogen atom, a linear, branched or cyclic (C1-C6) alkyl group which may have a substituent, a (C2-C6) alkynyl group which may have a substituent, and a (C7-C20) aralkyl group which may have a substituent. Examples of the substituent that may be carried by the alkyl group, alkynyl group, and aralkyl group include a hydroxy group, an amino group a formyl group, and a carboxy group.

In regard to the terminal group of the polyethylene glycol segment, examples of a linear alkyl group which may have a substituent include a methyl group, an ethyl group, an n-propyl group, an n-butyl group, an n-pentyl group, and an n-hexyl group. Examples of a branched alkyl group which may have a substituent include an isopropyl group an isobutyl group, a t-butyl group, an isopentyl group, a 2-methylbutyl group, a neopentyl group, a 1-ethylpropyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, and a 2-ethylbutyl group. Examples of a cyclic alkyl group which may have a substituent include a cyclopropyl group, a cyclobutyl group, a cyclopentyl group, and a cyclohexyl group.

In regard to the terminal group of the polyethylene glycol segment, examples of the substituent which may be carried by a linear alkyl group include a thiol group, a hydroxy group, a halogeno group, a nitro group, a cyano group, an alkylthio group, a carbocyclic or heterocyclic aryl group, an arylthio group, an alkylsulfinyl group, an arylsulfinyl group, an alkylsulfonyl group, a sulfamoyl group, an alkoxy group, an aryloxy group, an acyloxy group, an alkoxycarbonyloxy group, a carbamoyloxy group, a substituted or unsubstituted amino group, an acylamino group, an alkoxycarbonylamino group, a ureido group, a sulfonylamino group, a sulfamoylamino group, a formyl group, an acyl group, a carboxy group, an alkoxycarbonyl group, a carbamoyl group, and a silyl group.

In regard to the terminal group of the polyethylene glycol segment, examples of a (C2-C6) alkynyl group which may have a substituent include a 2-propynyl, a 3-butynyl group, a 4-heptynyl group, and a 5-hexynyl group.

In regard to the terminal group of the polyethylene glycol segment, a (C7-C20) aralkyl group which may have a substituent is a linear or branched alkyl group in which a hydrogen atom at any one site has been substituted with an aryl group. Examples include a benzyl group, a 2-phenylethyl group, a 4-phenylbutyl group, a 3-phenylbutyl group, a 5-phenylpentyl group a 6-phenylhexyl group, and an 8-phenyloctyl group. Preferred examples include a benzyl group, a 4-phenylbutyl group, and an 8-phenyloctyl group.

The other terminal group of the polyethylene glycol segment is a linking group for bonding to the polyamino acid derivative segment that will be described below. In General Formula (1) that will be described below, this linking group corresponds to A.

The linking group is not particularly limited as long as it is a group capable of linking two polymer segments by chemical bonding, and any linking group including functional groups that may be respectively bonded to a polyethylene glycol terminal group and a terminal group of a polyamino acid derivative is desirable. An example thereof is a (C1-C6) alkylene group having bondable functional groups as the terminal groups. Regarding the mode of linkage to the polyethylene glycol segment, an ether bond formed by a terminal oxygen atom of a polyoxyethylene group; ($CH_2CH_2O$) is preferred, and regarding the mode of linkage to the polyamino acid derivative segment, an amide bond or an ester bond is preferred. That is, the linking group is a —$(CH_2)_s$—NH— group or a —$(CH_2)_s$—CO— group (wherein s represents an integer from 1 to 6 in both cases).

The —$(CH_2)_s$— moiety may have a substituent, including a methylene group, an ethylene group, a trimethylene group, a butylene group, and a hexamethylene group, and particularly, an ethylene group, a trimethylene group, and an n-propylene group are preferred. Meanwhile, examples of the substituent for —$(CH_2)_s$— include a hydroxy group, a halogeno group, an amino group, an alkylamino group, a dialkylamino group, an alkoxy group, and an aryl group.

The polyamino acid includes two or more molecules polymerized therein. The number of units of the polyamino acid chain may be determined by an analysis by $^1$H-NMR, or by neutralization titration of a polyethylene glycol-poly (aspartic acid and/or glutamic acid) block copolymer before bonding a hydrophobic substituent or a signal group that will be described below to the block copolymer. The number of units of amino acid is 2 to 20, preferably 3 to 20, more preferably 5 to 20, and even more preferably 5 to 18. In General Formula (1) that will be described below, ($x_1+x_2+y_1+y_2+z$) represents the total number of amino acid units of the polyamino acid.

When the total number of amino acid units is 3 to 20 units, the block copolymer thus obtainable has self-associating properties, and the average molecular weight of the main chain polymer falls in 10 kDa. Thus, an enhancement of the imaging effect is achieved. It is preferable that the number of units of the polyamino acid chain is set as appropriate in consideration of the molecular weight of the block copolymer.

Regarding the amino acids that constitute the polyamino acid chain, it is desirable so long as one or more units of amino acids capable of introducing a signal group are included, and there are no particular limitations on other constituent components. Any of naturally occurring amino acids, synthetic amino acids, and side-chain modification products thereof may be used. Furthermore, any of the L-form, the D-form, and the racemates may be used. Examples thereof include glycine, alanine, β-alanine, leucine, phenylalanine, serine, threonine, tyrosine, aspartic acid, glutamic acid, lysine, arginine, histidine, ornithine, and cysteine. Furthermore, examples of amino acids having modified side chains include an alkyl ester of aspartic acid or glutamic acid, an aralkyl ester of aspartic acid or glutamic acid, an alkylamide of aspartic acid or glutamic acid, an aralkylamide of aspartic acid or glutamic acid, and an alkyloxycarbonyl lysine such as Boc-lysine. The polyamino acid chain may be formed from any one kind of these amino acids, or a mixture of a plurality of kinds of amino acids may construct the segment.

Regarding the amino acid capable of introducing a signal group, it is preferable to use an amino acid having a bondable functional group such as a carboxy group, an amino group, a hydroxy group, or a sulfhydryl group in a side chain. That is, when signal groups are introduced into these bondable functional groups by chemical bonding, the hydrophobic polymer segment may be constructed. Examples of the amino acid include aspartic acid, glutamic acid, lysine, arginine, histidine, ornithine, serine, threonine, tyrosine, and cysteine.

The polyamino acid chain of the hydrophobic polymer segment containing a polyamino acid chain having a substituent in a side chain in the block copolymer of the present invention is an amino acid chain such as polyglutamic acid, polyaspartic acid, polylysine, polyornithine, polytyrosine, polyserine, or polythreonine. Preferably, a polyaspartic acid or polyglutamic acid having a carboxy group as a reactive substituent that is capable of introducing a substituent into a side chain, may be mentioned. These polyamino acids having side-chain carboxy groups may be α-amide bond type polymers, may be amide bond type polymers having a side-chain carboxy group bonded thereto by an amide bond, may be β-amide bond type polymers, or mixtures thereof. Furthermore, the polyamino acid segment may be a linear polyamino acid segment, or may be a segment having a branched structure having side chains.

It is preferable that the polyamino acid chain is a polyamino acid chain constructed from aspartic acid and/or glutamic acid since such polyamino acid chain contains an aspartic acid derivative and/or a polyglutamic acid derivative, both having a substituent bonded to a side-chain carboxy group. More preferably, a polyaspartic acid chain constructed only from aspartic acid, or a polyglutamic acid chain constructed only from glutamic acid is preferred. That is, in a case in which the polyamino acid chain contains an aspartic acid chain having a substituent bonded to a side-chain carboxy group, it is preferable to employ a polyaspartic acid chain, and in a case in which the polyamino acid chain contains a glutamic acid chain having a substituent bonded to a side-chain carboxy group, it is preferable to employ a polyglutamic acid chain. The mode of polymerization of polyaspartic acid or polyglutamic acid is a peptide bond, and the polyamino acid may be an α-bonded product, a β-bonded product, or a γ-bonded product, or may be a mixture thereof.

One terminal of the hydrophobic polymer segment containing the polyamino acid chain is bonded to the polyethylene glycol segment described above. The other terminal group may be an N-terminal group or a C-terminal group, and may be an unprotected free amino group, a free carboxylic acid, or a salt thereof. The terminal group may also be a modification product having an appropriately modified N-terminal group or an appropriately modified C-terminal group. Preferred is a product having a modified N-terminal group or a modified C-terminal group.

Examples of the modification product of the N-terminal group include an acylamide type modification product, an alkoxycarbonylamide type modification product (urethane type modification product), and an alkylaminocarbonylamide type modification product (urea type modification product). Meanwhile, examples of the modification product of the C-terminal group include an ester type modification product, an amide type modification product, and a thioester type modification product.

The modifying group for the N-terminal group and the C-terminal group may be any modifying group, and preferred examples include terminal modifying groups such as a linear, branched or cyclic (C1-C6) alkyl group which may have a substituent, a (C6-C18) aromatic group which may have a substituent, and a (C7-C20) aralkyl group which may have a substituent, all of which are to be bonded to the N-terminal group and the C-terminal group via an appropriate bonding group.

That is, the N-terminal group is preferably an appropriate acylamide type modification product or an alkoxycarbonylamide type modification product (urethane type modification product), and is preferably a linear, branched or cyclic (C1-C6) alkyl group which may have a substituent, a (C6-C18) aromatic group which may have a substituent, or a (C7-C20) aralkyl group which may have a substituent, all of them being linked via a carbonyl group or a carbonyloxy group.

Examples for the N-terminal group which is an acylamide type modification product (in General Formula (1) that will be described below, corresponds to $R_2$) is a (C1-C6) acyl group which may have a substituent, specifically including a linear, branched or cyclic (C1-C6) acyl group which may have a substituent. Such substituent contains a hydroxy group, a halogeno group, an amino group, an alkylamino group, a dialkylamino group, an alkoxy group, an aryl group, or the like. Examples of the (C1-C6) acyl group include a formyl group, an acetyl group, a trichloroacetyl group, a trifluoroacetyl group, a propionyl group, a pivaloyl group, a benzylcarbonyl group, and a phenethylcarbonyl group. A linear, branched or cyclic (C1-C4) acyl group which may have a substituent is more preferred, and an acetyl group, a trichloroacetyl group, and a trifluoroacetyl group are more preferred.

Examples for the N-terminal group as an alkoxycarbonylamide type modification product (in General Formula (1) that will be described below, corresponds to $R_2$) is a (C1-C6) alkoxycarbonyl group which may have a substituent, specifically including a linear, branched or cyclic (C1-C6) alkoxycarbonyl group which may have a substituent. Such substituent contains a hydroxy group, a halogeno group, an amino group, an alkylamino group, a dialkylamino group, an alkoxy group, an aryl group, or the like. Examples of the (C1-C6) alkoxycarbonyl group include a methoxycarbonyl group, an ethoxycarbonyl group, a t-butoxycarbonyl group, a benzyloxycarbonyl group, and a 9-fluorenylmethyloxycarbonyl group.

Meanwhile, the C-terminal group is preferably an appropriate amide type substituent or an appropriate ester type substituent, specifically including a linear, branched or cyclic (C1-C8) alkyl group which may have a substituent, a (C6-C18) aromatic group which may have a substituent, or a (C7-C20) aralkyl group which may have a substituent, all of them being linked via an amide group or an ester group.

Examples of the linear, branched or cyclic (C1-C6) alkyl group which may have a substituent for the terminal group include a methyl group, an ethyl group, an n-propyl group, an isopropyl group, an n-butyl group, a t-butyl group, and a cyclohexyl group.

Examples of a (C6-C18) aromatic group which may have a substituent for the terminal group include a phenyl group, a pyridyl group, and a naphthyl group.

A (C7-C20) aralkyl group which may have a substituent for the terminal group is a linear or branched alkyl group in which a hydrogen atom at any one site has been substituted with an aryl group. Examples thereof include a benzyl group, a 2-phenylethyl group, a 4-phenylbutyl group, and an 8-phenyloctyl group.

The hydrophobic polymer segment may contain a polyamino acid unit in which the above-described substituent is not bonded to a side chain of the polyamino acid chain. In a case in which the side chain is a carboxy group, the carboxy group may be in the form of free acid, or may be in the form of a pharmaceutically acceptable carboxylic acid salt. Examples of such carboxylic acid salt include lithium salt, sodium salt, potassium salt, magnesium salt, calcium salt, and ammonium salt.

According to the present invention, the substituent that is bonded to a side chain of the polyamino acid chain in the hydrophobic polymer segment is not particularly limited as long as the substituent does not inhibit or does promotes the nanoparticle-forming ability by which the block copolymer exhibits self-associating properties in an aqueous solution, and is capable of controlling the physical properties of the block copolymer. For example, when a hydrophobic group is introduced as the substituent, hydrophobicity of the polyamino acid derivative segment of the block copolymer may be increased. Meanwhile, when a hydrophilic substituent including an ionic functional group that is capable of forming a salt, such as an amino group, a carboxy group, or a hydroxy group, is introduced as the above-described substituent, hydrophilicity of the block copolymer may be increased.

According to the present invention, a signal group is a group having the characteristics that enable imaging by detection, and is a substance containing a fluorescent group, a radioisotope-containing group, a magnetic group, or the like. $R_3$ in General Formula (1) that will be described below is a signal group.

The fluorescent group includes, but not particularly limited, groups derived from a fluorescein-based dye, an indocyanine-based dye, a rhodamine-based dye, a BODIPY-based dye, a xanthene-based dye, a Nile Red-based dye, and a quantum dot. Among them, a fluorescent group having an amino group is preferred, and examples thereof include 2-(2-aminoethoxy)-9-(diethylamino)-5H-benzo[a]phenoxazin-5-one, BODIPY (registered trademark) TR Cadaverine, BODIPY (registered trademark) FL Ethylenediamine, ALEXA FLUOR (registered trademark) 594 Cadaverine, TEXAS RED (registered trademark) Cadaverine, and ATTO 594 amine.

The radioisotope-containing group includes, but not particularly limited, groups derived from a sugar, an amino acid, and a nucleic acid, all being labeled with radioisotopes such as 18F.

The magnetic group includes, but not particularly limited, a group having a magnetic body such as ferrichrome, ferrite nanoparticles, and magnetic nanoparticles.

The hydrophobic substituent according to the present invention is a moiety that enhances the nanoparticle-forming ability by which the block copolymer exhibits self-associating properties in an aqueous solution, and does not bring about any interruption to the imaging effect of the signal group that will be described below or the active ingredient of the pharmaceutical product. Particularly, the hydrophobic substituent is an optional substituent that is used to introduce a hydrophobic substituent into the polyamino acid chain together with a signal group and to adjust the degree of hydrophobicity of the hydrophobic polymer segment, in a case in which the polyamino acid chain does not acquire sufficient hydrophobicity against the hydrophilic polymer segment containing a polyethylene glycol chain merely by means of the bonding of the signal group. Such a hydrophobic substituent may be used without any particular limitations, and it is still acceptable that a plurality of kinds of hydrophobic substituents exist in one molecule of the block copolymer. The hydrophobic substituent is preferably an ester derivative and/or an amide derivative, both having an appropriate substituent. $R_4$ in General Formula (1) that will be described below is a hydrophobic substituent and/or a hydroxy group.

The hydrophobic substituent specifically represents one or more substituents selected from the group consisting of a linear, branched or cyclic (C1-C30) alkoxy group which may have a substituent, a linear, branched or cyclic (C1-C30) alkylamino group which may have a substituent, a linear, branched or cyclic (C1-C30) dialkylamino group, a (C1-C8) alkylaminocarbonyl-(C1-C8) alkylamino group which may have a substituent, a physiologically active substance having a hydroxy group and/or an amino group, and a hydroxy group. The hydrophobic substituents may be all the same, or there may be a plurality of kinds of hydrophobic substituents.

A linear, branched or cyclic (C1-C30) alkoxy group which may have a substituent with regard to the hydrophobic substituent is a product in which an ester type modifying group is bonded to a side-chain carboxy group of the poly(aspartic acid and/or glutamic acid) segment. Such substituent may include a hydroxy group, a halogeno group, an amino group, an alkylamino group, a dialkylamino group, an alkoxy group, an aryl group, or the like. Examples of the (C1-C30) alkoxy group for $R_4$ include a methoxy group, an ethoxy group, a 1-propyloxy group, an isopropyloxy group, an n-butoxy group, a t-butoxy group, a cyclohexyloxy group, a benzyloxy group, a 4-phenylbutyloxy group, an n-octyloxy group, a decyloxy group, a dodecyloxy group, a tetradecyloxy group, a hexadecyloxy group, an octadecyloxy group, an eicosyloxy group, a docosyloxy group, a tetracosyloxy group, a hexacosyloxy group, an octacosyloxy group, and a triacontyloxy group.

A linear, branched or cyclic (C1-C30) alkylamino group which may have a substituent with regard to the hydrophobic substituent is a product in which an alkylamide type modifying group is bonded to a side-chain carboxy group of the poly(aspartic acid and/or glutamic acid) segment. Such substituent may include a hydroxy group, a halogeno group, an amino group, an alkylamino group, a dialkylamino group, an alkoxy group, an aryl group, or the like. Examples of the (C1-C30) alkylamino group for $R_4$ include a methylamino group, an ethylamino group, a propylamino group, an isopropylamino group, a butylamino group, a t-butylamino group, a cyclohexylamino group, a benzylamino group, a 4-phenylbutylamino group, an octylamino group, a decylamino group, a dodecylamino group, a tetradecylamino group, a hexadecylamino group, an octadecylamino group, an eicosylamino group, a docosylamino group, a tetracosylamino group, a hexacosylamino group, an octacosylamino group, and a triacontylamino group.

Furthermore, an amino acid having a protected carboxy group is also included in the (C1-C30) alkylamino group which may have a substituent. Examples of the amino acid having a protected carboxy group that may be used include glycine methyl ester, glycine benzyl ester, β-alanine methyl ester, β-alanine benzyl ester, alanine methyl ester, leucine methyl ester, valine benzyl ester, phenylalanine methyl ester, and phenylalanine benzyl ester.

The linear, branched or cyclic (C1-C30) dialkylamino group which may have a substituent with regard to the hydrophobic substituent is a product in which a dialkylamide type modifying group is bonded to a side-chain carboxy group of the poly(aspartic acid and/or glutamic acid) segment. Such substituent may include a hydroxy group, a halogeno group, an amino group, an alkylamino group, a dialkylamino group, an alkoxy group, an aryl group, or the like. Examples of the di(C1-C30) alkylamino group for $R_4$ include a dimethylamino group, a diethylamino group, a dipropylamino group, a diisopropylamino group, a dibutylamino group, a pyrrolidino group, a piperidino group, a dibenzylamino group, an N-benzyl-N-methylamino group, a dioctylamino group, a dinonylamino group, a didecylamino group, a didodecylamino group, a ditetradecylamino group, a dihexadecylamino group, a dioctadecylamino group, and a dieicosylamino group.

The (C1-8) alkylaminocarbonyl-(C1-8) alkylamino group which may have a substituent with regard to the hydrophobic substituent is a product in which a urea type modifying group is bonded to a side-chain carboxy group of the poly(aspartic acid and/or glutamic acid) segment. The alkyl groups may be groups of the same kind, or groups of different kinds. Such substituent may include a hydroxy group, a halogeno group, an amino group, an alkylamino group, a dialkylamino group, an alkoxy group, an aryl group, or the like. In the case of having a substituent, a dialkylamino group is preferred. Examples of the (C1-C8) alkylaminocarbonyl-(C1-C8) alkylamino group which may have a substituent include a methylaminocarbonylmethylamino group, an ethylaminocarbonylethylamino group, an isopropylaminocarbonylisopropylamino group, a cyclohexylaminocarbonylcyclohexylamino group, an ethylaminocarbonyl-(3-dimethylaminopropyl)amino group, and a (3-dimethylaminopropyl)aminocarbonylethylamino group.

Since it is also purported to use the present invention as a pharmaceutical product, an active ingredient of a pharmaceutical product may be used as the hydrophobic substituent. Regarding the active ingredient of a pharmaceutical product, it is preferable to use a known pharmaceutically active ingredient or a pharmaceutically active ingredient candidate compound, both having a hydroxy group and/or an amino group. Furthermore, as the physiologically active substance having a hydroxy group and/or an amino group, any substance containing a known pharmaceutically active ingredient or a pharmaceutically active ingredient candidate compound may be applied without any particular limitations. That is, the pharmaceutically active ingredient or a candidate compound thereof may be applied as the physiologically active substance having a hydroxy group and/or an amino group by converting the pharmaceutically active ingredient or a candidate compound into a derivative or a prodrug and introducing a hydroxy group and/or an amino group thereinto.

The physiologically active substance according to the present invention means an active ingredient of a known pharmaceutical product, or a pharmaceutically active ingredient candidate compound, used for the treatment of a disease such as a malignant tumor disease, an inflammatory disease, or an infectious disease, or an active ingredient obtained by converting the aforementioned active ingredient or candidate compound into a derivative or a prodrug.

Examples of a physiologically active substance that is used for malignant tumor diseases include camptothecin derivatives such as 7-ethyl-10-hydroxycamptothecin, irinotecan, nogitecan, and 9-aminocamptothecin; taxane derivatives such as paclitaxel, docetaxel, and cabazitaxel; resorcinol derivatives having HSP90 inhibitory activity, such as ganetespib and luminespib; anthracycline derivatives such as doxorubicin, epirubicin, amrubicin, daunorubicin, idarubicin, and pirarubicin; ramapycin derivatives such as sirolimus, everolimus, and temsirolimus; cytidine-based antimetabolites such as gemcitabine, cytosine arabinoside, enocitabine, cytarabine ocfosfate, ethynylcytidine, azacitidine, and decitabine; folic acid antimetabolites such as methotrexate, pemetrexed, levofolinate, and folinate; purine-based antimetabolites such as fludarabine, nelarabine, pentostatin, and cladribine; pyrimidine fluoride-based antimetabolites such as doxifluridine, capecitabine, tefugar, fluorouracil, and carmofur; platinum-containing compounds such as cisplatin, carboplatin, oxaliplatin, and nedaplatin; mitomycin derivatives such as mitomycin C; bleomycin derivatives such as bleomycin and libromycin; vinca alkaloid derivatives such as vincristine, vinblastine, vindesine, and vinorelbine; podophyllotoxin derivatives such as etoposide and teniposide; halichondrin derivatives such as eribulin; staurosporine derivatives such as rebeccamycin and UCN-01; thalidomide derivatives such as lenalidomide and pomalidomide; vitamin A derivatives such as tretinoin and tamibarotene; proteasome inhibitors such as bortezomib, carfilzomib, and ixazomib; combretastatin derivatives such as combretastatin A4; MEK inhibitors such as binimetinib, cobimetinib, and trametinib; CDK inhibitors such as dinaciclib, flavopiridol, and palbociclib; Raf kinase inhibitors such as dabrafenib, sorafenib, and vemurafenib; HDAC inhibitors such as vorinostat, belinostat, panabinostat, and romidepsin; actin polymerization inhibitors such as cytochalasin, latrunculin, and phalloidin; PARP inhibitors such as veliparib, rucaparib, and olaparib; tyrosine kinase inhibitors such as crizotinib, imatinib, gefitinib, erlotinib, apatinib, dasatinib, bosutinib, vandetanib, sunitinib, axitinib, pazopanib, lenvatinib, lapatinib, nintedanib, nilotinib, ceritinib, alectinib, ruxolitinib, crizotinib, and ibrutinib; nitrogen mustard-based alkylating agents such as bendamustine, cyclophosphamide, ifosfamide, bulusfan, melphalan; nitrosourea-based alkylating agents such as nimustine, ranimustine, and lomustine; alkylating agents such as dacarbazine, temozolomide, procarbazine, and thiotepa; aromatase inhibitors such as anastrozole, exemestane, letrozole, and fadrozole; anti-androgenic agents such as hydroxyflutamide, flutamide, bicalutamide, and enzaltamide; CYP17 (lyase) inhibitors such as abiraterone; anti-estrogenic agents such as tamoxifen and toremifene; and hormonal agents such as estramustine, progesterone, mitotane, and medroxyprogesterone.

Examples of a physiologically active substance that is used for inflammatory diseases include tacrolimus derivatives such as tacrolimus; steroid derivatives such as dexamethasone and prednisolone; ramapycin derivatives such as sirolimus, everolimus, and temsirolimus; immunosuppressants such as cyclosporine, fingolimod, azathioprine, mizoribine, myrcophenolate mofetil, and gusperimus; and NSAIDs such as diflunisal and tiaramide.

Examples of the physiologically active substance that is used for infectious diseases include antifungal agents, such as polyene-based antibiotic substances such as amphotericin B and nystatin, azole-based derivatives such as fluconazole and voriconazole, candin-based derivatives such as micafungin, and pyrimidine derivatives such as flucytosine; and antiviral agents such as acyclovir, valacyclovir, and ganciclovir; and antiviral agents such as zanamivir, oseltamivir, and laninamivir.

The block copolymer of the present invention has performance with enhanced migration characteristics and penetrability into a target tissue and enhanced excretability through the kidneys and the like. Consequently, the block copolymer provides effects of promoting the distribution of a signal group in a diseased target tissue or sensitization of a physiologically active substance, enhancing an imaging ability or a pharmacological effect, and reducing adverse side effects by suppressing the distribution of a signal group in normal tissues or sensitization of a physiologically active substance. Therefore, it is preferable to apply the block copolymer to a disease for which reduction of side effects in normal tissues is required, and it is preferable to use the block copolymer for a malignant tumor disease or an inflammatory disease. The block copolymer has superior migration characteristics to a tissue such as a tumor or an inflammation site and superior penetrability into the interior of a tissue, and exhibits an enhanced imaging ability or pharmacological effect in a tumor or an inflammation site. Furthermore, since the block copolymer also exhibits excretability through the kidneys or the like, the in vivo retention characteristics shown by a polymeric DDS preparation are well controlled, and undesirable migration to normal tissues may be suppressed. Accordingly, reduction of adverse side effects may be achieved.

The average molecular weight of the main chain polymer combining a polyethylene glycol chain and a polyamino acid chain of the present invention is not less than 2 kDa and not more than 10 kDa. Regarding this average molecular weight, a calculated value obtained by summing the various constituent molecular weights of the constituent moieties of the main chain polymer is employed. That is, a calculated value obtained by summing the (1) average molecular weight of the polyethylene glycol chain and the (2) average molecular weight of the polymer main chain portion of the polyamino acid chain excluding the signal group and the optional hydrophobic substituent, is employed as the average molecular weight.

Meanwhile, the average molecular weight of the main chain polymer combining a polyethylene glycol chain and a polyamino acid chain may be described with accuracy to the nearest kDa unit. In the following description, a preferable analysis method for the various constituent moieties will be described; however, the analysis methods are not particularly limited. Any analysis method with sufficiently accurate for the measurement of the molecular weight of the polyamino acid derivative to the nearest kDa unit may be used without any particular limitations.

The (1) average molecular weight of the polyethylene glycol chain is a measured value of the molecular weight of the polyethylene glycol compound that constructs the polyethylene glycol segment. The average molecular weight that may be determined from the peak top molecular weight measured by a GPC method based on polyethylene glycol standards is employed, and as a calculated value, a value rounded off to the nearest hundred is used.

The (2) average molecular weight of the main chain portion of the polyamino acid chain is a calculated value obtained by multiplying the average molecular weight of the polymerized monomer unit of the polyamino acid chain by the average number of units. Regarding the number of units, a number of units calculated by a method of quantitatively determining side-chain carboxy groups of the polyamino acid by neutralization titration, or calculated from the integral values of $^1$H-NMR, may be used. It is preferable to use a neutralization titration method.

The block copolymer of the present invention preferably has the mass content percentage of the polyethylene glycol segment of not less than 10% by mass and not more than 80% by mass. That is, it is preferable that the proportion occupied by the molecular weight corresponding to the polyethylene glycol segment in the molecular weight of the block copolymer is not less than 10% by mass and not more than 80% by mass. When the mass content percentage of the polyethylene glycol segment is less than 10% by mass, water-solubility is markedly decreased, and there is a risk that nanoparticles may not be formed by self-association in an aqueous solution. Meanwhile, when the mass content percentage of the polyethylene glycol segment is more than 80% by mass, since the block copolymer is configured to include a reduced proportion of the polyamino acid derivative segment that is responsible for self-associating properties, there is a risk that the nanoparticle-forming properties based on hydrophobic interaction may be reduced. It is preferable to set the mass content percentage of the polyethylene glycol segment for the block copolymer of the present invention so as to allow an imaging function to be exhibited sufficiently and to optionally obtain a therapeutic effect by achieving efficacy and reduction of adverse side effects.

The mass content percentage of the polyethylene glycol segment is more preferably not less than 20% by mass and not more than 70% by mass. It is particularly preferable that the mass content percentage is not less than 30% by mass and not more than 65% by mass.

It is preferable for the block copolymer of the present invention that the mass content percentage of the signal group and the optional hydrophobic substituent is not less than 5% by mass and not more than 50% by mass. In order to obtain appropriate associating properties for the block copolymer of the present invention, the total mass of substituents obtained by summing the masses of the signal group and the optional hydrophobic substituent in the hydrophobic polymer segment is an important parameter. That is, when the percentage content of the signal group and the optional hydrophobic substituent is less than 5% by mass, water-solubility is markedly decreased, and there is a risk that nanoparticles may not be formed by self-association in an aqueous solution. Meanwhile, when the percentage content of the signal group and the optional hydrophobic substituent is more than 50% by mass, the balance of the self-associating properties of the block copolymer is markedly lowered, and there is a risk that desired nanoparticle-forming properties may not be exhibited.

The mass content percentage of the signal group and the optional hydrophobic substituent is preferably not less than 7% by mass and not more than 50% by mass, and more preferably not less than 8% by mass and not more than 50% by mass.

The nanoparticles formed by the block copolymer of the present invention or a composition including the block copolymer exhibit self-associating properties in an aqueous solution.

The particle size (average particle size) of the nanoparticles of the present invention is 1 nm to 30 nm. Preferably, the particle size is less than 20 nm, and not less than 1 nm and less than 20 nm.

The particle size (average particle size) of the nanoparticles according to the invention is measured by, for example, an induced diffraction grating method. An induced diffraction grating method is a method of: (1) irradiating a 1 or 2 mg/mL aqueous solution of the block copolymer of the present invention or a composition including the block copolymer with laser light, thereby forming diffraction gratings by dielectrophoresis; (2) stopping an external force that causes dielectrophoresis, measuring the annihilation rate of the diffraction gratings caused by diffusion, and (3) applying the annihilation rate to the Stokes-Einstein relational equation to obtain the particle size. For example, the particle size may be measured with a single nanoparticle size measuring apparatus, IG-1000, manufactured by Shimadzu Corp.

Since the block copolymer of the present invention or a composition including the block copolymer is a block copolymer in which a hydrophobic polymer segment containing a hydrophilic polyethylene glycol chain is linked to a hydrophobic polymer segment containing a polyamino acid chain having a signal group and an optional hydrophobic substituent in a side chain, it is considered that the hydrophobic polymer segments of a plurality of block copolymer molecules will associate with one another in an aqueous solution based on hydrophobic interaction. As a result, it is speculated that the block copolymer form micelle-like associates having a core-shell structure in which the hydrophobic polymer segment forms the inner core (core part), and the hydrophilic polyethylene glycol segment covers the periphery of the inner core and forms an outer shell layer (shell part), and these micelle-like associates are observed as the aforementioned nanoparticles.

One type of the block copolymer of the present invention is represented by the following General Formula (1).

[Chemical Formula 2]

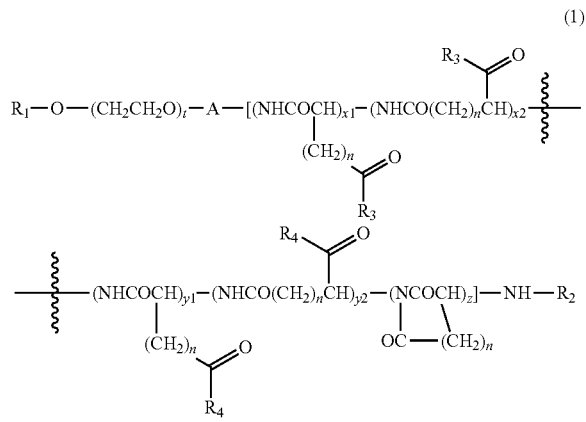

wherein $R_1$ represents a hydrogen atom or a linear, branched or cyclic (C1-C6) alkyl group which may have a substituent; t represents an integer from 20 to 140; A represents a (C1-C6) alkylene group which may have a substituent; $R_2$ represents a substituent selected from the group consisting of a hydrogen atom, a (C1-C6) acyl group, and a (C1-C6) alkoxycarbonyl group; $R_3$ represents the above-described signal group; $R_4$ represents the above-described hydrophobic substituent; n represents 1 or 2; $x_1$, $x_2$, $y_1$, $y_2$, and z each independently represent an integer from 0 to 20; $(x_1+x_2)$ represents an integer from 1 to 10; $(x_1+x_2+y_1+y_2+z)$ represents an integer from 3 to 20; and the various constituent units to which $R_3$ and $R_4$ are bonded, and a constituent unit formed by intramolecular cyclization of a side-chain carbonyl group constitute a structure with those constituent units being each independently randomly arranged.

Examples of $R_1$ include a methyl group, an ethyl group, an n-propyl group, an isopropyl group, an n-butyl group, an s-butyl group, a t-butyl group, a benzyl group, a 2,2-dimethoxyethyl group, a 2,2-diethoxyethyl group, and a 2-formylethyl group. Particularly, a methyl group, an ethyl group, an n-propyl group, an isopropyl group, an n-butyl group, an s-butyl group, a t-butyl group, and the like are preferred.

In General Formula (1), $x_1$, $x_2$, $y_1$, $y_2$, and z each represent the number of units of the constituent units of the aspartic acid derivative unit and/or glutamic acid derivative unit in the poly(aspartic acid and/or glutamic acid) segment in the block copolymer, and they each represents an integer from 0 to 20.

In General Formula (1), $(x_1+x_2)$ represents the total number of aspartic acid units and/or glutamic acid units having $R_3$ bonded thereto. $(x_1+x_2)$ is an integer from 1 to 10. Preferably, $(x_1+x_2)$ is an integer from 1 to 9, and more preferably an integer from 1 to 8. The proportion of $(x_1+x_2)$ with respect to $(x_1+x_2+y_1+y_2+z)$, which is the number of units of the poly(aspartic acid and/or glutamic acid) derivative segment, is 1% to 80%, preferably 1% to 70%, and more preferably 1% to 60%.

The number of units of aspartic acid units and/or glutamic acid units, both having $R_3$ bonded thereto, is calculated from the amount of bonding of $R_3$ and the number of units of the poly(aspartic acid and/or glutamic acid) chain. The amount of bonding of $R_3$ may be determined by a method of cleaving $R_3$ from the block copolymer to which $R_3$ is bonded, and quantitatively analyzing $R_3$ thus released. A method of calculating the number of units from the reaction ratio of $R_3$ at the time of producing the block copolymer having $R_3$ bonded thereto may also be used.

In regard to General Formula (1), $(y_1+y_2)$ represents the total number of aspartic acid units and/or glutamic acid units, both having $R_4$ bonded thereto. Furthermore, z represents the total number of aspartic acid units and/or glutamic acid units, both having a structure in which a side-chain carboxy group has been intramolecularly cyclized. $(y_1+y_2)$ and z each represents an integer from 0 to 19. Preferably, $(y_1+y_2)$ and z each represents an integer from 1 to 18. The proportion of $(y_1+y_2+z)$ with respect to $(x_1+x_2+y_1+y_2+z)$, which is the number of polymerization units of the poly (aspartic acid and/or glutamic acid) derivative segment, is 20% to 99%, and preferably 30% to 99%.

The number of units of aspartic acid unit and/or glutamic acid unit, to which $R_4$ is bonded, is calculated from the amount of bonding of $R_4$ and the number of polymerization units of the poly(aspartic acid and/or glutamic acid) segment. The amount of bonding of $R_4$ may be determined by a method of cleaving $R_4$ from the block copolymer and quantitatively analyzing $R_4$ thus released. A method of calculating the reaction ratio of $R_4$ at the time of producing the block copolymer may also be used. The number of units may also be calculated from the integral values of $^1$H-NMR.

In regard to a block copolymer having $R_3$ and $R_4$ bonded thereto as represented by General Formula (1) according to the present invention, the poly(aspartic acid and/or glutamic acid) segment is a polymer segment in which aspartic acid units and/or glutamic acid units, to which $R_3$ and $R_4$ are bonded, and aspartic acid units and/or glutamic acid units having a structure in which a side-chain carboxy group has been intramolecularly cyclized, exist as a mixture. The respective constituent units exist in two or more units, and the arrangement thereof is not particularly controlled and irregularly arranged. Thus, the poly(aspartic acid and/or glutamic acid) segment has a segment structure in which the constituent units are arranged randomly.

The block copolymer represented by General Formula (1) is preferably such that the mass content percentage of the substituents represented by $R_3$ and optionally $R_4$ is not less than 5% by mass and not more than 50% by mass. Both in the case in which the content of the substituents represented by $R_3$ and optionally $R_4$ is lower than 5% by mass, and in the case in which the content of $R_3$ and optionally $R_4$ is higher than 50% by mass, the hydrophilicity-hydrophobicity balance of the block copolymer having $R_3$ and optionally $R_4$ bonded thereto is largely changed, and there is a risk that the block copolymer may not have suitable self-associating properties and may not exhibit desired pharmacokinetics. The mass content percentage of the substituents represented by $R_3$ and optionally $R_4$ is preferably not less than 7% by mass and not more than 50% by mass, and more preferably not less than 8% by mass and more than 50% by mass.

A method for producing the block copolymer represented by General Formula (1) will be explained. The following methods may be mentioned; a method of producing a block copolymer having the polyethylene glycol segment of the present block copolymer linked to a polyamino acid segment containing aspartic acid and/or glutamic acid, and introducing substituent component components corresponding to $R_3$ and optional $R_4$ to this block copolymer by condensation reactions; a method of bonding a polymer component containing a polyethylene glycol segment to a polyamino acid derivative having a signal group or a hydrophobic substituent bonded thereto; and the like. The former method is preferably; producing in advance a block copolymer having a polyethylene glycol segment linked to a polyamino acid segment, and introducing substituent component compounds corresponding to $R_3$ and optionally $R_4$ into this block copolymer by condensation reactions is preferred.

Regarding the method for producing the block copolymer having a polyethylene glycol segment linked to a polyamino acid segment, a method of constructing a polyamino acid segment by performing polymerization in sequence using amino acid-N-carboxyanhydrides to be used for a compound containing a polyethylene glycol segment; a method of bonding a polyethylene glycol segment to a polyamino acid segment; and the like may be mentioned. From the viewpoint that the reactivity of amino acid-N-carboxyanhydrides is high, and that it is easy to control the number of polyamino acid units, it is preferable to use the former method.

An embodiment will be explained for the production method for obtaining the block copolymer according to the present invention by producing in advance a block copolymer having a polyethylene glycol segment linked to a polyamino acid derivative segment, and bonding $R_3$ and $R_4$ to this block copolymer.

First, a polyethylene glycol derivative having an amino group at one terminal (for example, methoxy polyethylene glycol-1-propylamine) is sequentially reacted with amino acid-N-carboxyanhydrides in which a side-chain functional group of the amino acid is appropriately protected, and the skeleton of a block type copolymer having a polyethylene glycol segment linked to a polyamino acid segment is constructed in sequence by polymerization. In this case, aspartic acid and/or glutamic acid may be incorporated into the polyamino acid segment by appropriately incorporating aspartic acid-N-carboxyanhydride and/or glutamic acid-N-carboxyanhydride, both having a protected side-chain carboxy group, as the amino acid-N-carboxyanhydride. Subsequently, an appropriate deprotection reaction is carried out, and thus the block copolymer containing aspartic acid and/or glutamic acid, in which the side-chain carboxy group has been deprotected, may be prepared. In a case in which the side-chain carboxy group is a benzyl ester, a deprotection reaction may be carried out by hydrolysis under alkaline conditions or by a hydrogenolysis reaction.

It is only desirable that this polyethylene glycol-polyamino acid block copolymer is reacted with $R_3$ and $R_4$ under condensation conditions in an appropriate reaction solvent.

In the condensation reaction between the polyethylene glycol-polyamino acid block copolymer and $R_3$ and $R_4$, regarding the solvent that may be used, any solvent may be used without particular limitations as long as both the compounds are dissolved. For example, water-soluble organic solvents such as N,N-dimethylformamide (DMF), N-methylpyrrolidone (NMP), and 1,3-dimethyl-2-imidazolidinone (DMI) may be mentioned. These solvents may be used singly or may be used as mixed solvents thereof. Furthermore, mixed solvents of the above-described solvents with other organic solvents may also be used.

Furthermore, regarding the condensing agent to be used, any conventional dehydration condensing agent may be used without any particular problem as long as that causes an esterification reaction based on a dehydration condensation reaction between a carboxylic acid and a hydroxy group, and/or an amidation reaction based on a dehydration condensation reaction between a carboxylic acid and an amino group. Such condensing agent may include carbodiimide-based condensing agents such as dicyclohexylcarbodiimide (DCC), diisopropylcarbodiimide (DIPCI), and 1-ethyl-3-(3-dimethylaminopropyl)carbodiimide hydrochloride (WSC); triazine-based condensing agents such as 4-(4,6-dimethoxy-1,3,5-triazin-2-yl)-4-methylmorpholium chloride n-hydrate (DMT-MM); 1-ethoxycarbonyl-2-ethoxy-1,2-dihydroquinoline (EEDQ), and di-tert-butyl dicarbonate ($Boc_2O$). At the time of the condensation reaction, reaction aids such as 4-dimethylaminopyridine (DMAP), 1-hydroxybenzotriazole (HOBt), and N-hydroxysuccinimide (HOSu) may also be used. When a carbodiimide-based condensing agent is used, in $R_4$ of General Formula (1), a (C1-C8) alkylaminocarbonyl-(C1-C8) alkylamino group which may have a substituent may be introduced simultaneously with $R_3$ and $R_4$.

Regarding the reaction, the condensation reaction may be carried out usually at a temperature of 0° C. to 180° C., and preferably 5° C. to 100° C.

Another $R_4$ such as the aforementioned (C1-C30) alkoxy group, the (C1-C30) alkylamino group, or the di(C1-C30) alkylamino group, may be introduced into the polyamino acid segment for the purpose of regulating the self-associating properties of the block copolymer of the present invention. Such method may include a method of activating carboxy groups of a polyethylene glycol-polyamino acid copolymer by adding a condensing agent, and then reacting an alcohol compound and an amino compound, which corresponds to $R_4$ that is intended to be introduced, at a desired equivalent amount; or a method of activating the alcohol compound or the amino compound and then reacting the activated compound with the polyamino acid segment of the copolymer.

In this case, the signal group may be introduced after $R_4$ is introduced by means of the alcohol compound or the amino compound, or the reverse is also acceptable. It is also acceptable to introduce $R_3$ and $R_4$ simultaneously.

$R_4$ may be a substituent of a single kind or may be a plurality of kinds of substituents. In a case in which a plurality of kinds of substituents is to be introduced, when a mixture of various $R_4$'s may be synthesized by repeatedly reacting different alcohol compounds or amino compounds.

The block copolymer of the present invention may be produced by introducing $R_3$ as a signal group, and a physiologically active substance or a hydrophobic substituent as an optional hydrophobic substituent $R_4$ into a polyethylene glycol-polyamino acid block copolymer and then optionally performing conventional separation operations or purification operations.

A composition including the block copolymer of the present invention may be formed by, for example, mixing the block copolymer with a hydrophobic substance such as a physiologically active substance, or mixing a plurality of block copolymers with a hydrophobic substance such as a physiologically active substance, in an aqueous solution, and causing the mixture to self-assemble into a micelle form. Furthermore, the composition may also be formed by, for example, dissolving the block copolymer or a hydrophobic substance in an organic solvent and dialyzing the solution. Moreover, the composition may also be formed by, for example, dissolving these block copolymers or a hydrophobic substance in an organic solvent, mixing the solvent to become uniform, distilling off the solution under reduced pressure to obtain a film of the polymers, adding water to the film thus obtained, mixing the film of the polymers with water, and causing the mixture to self-assemble into a micelle form.

Example of the organic solvent include methanol, acetone, acetonitrile, and N,N-dimethylformamide.

The aqueous solution may be formed by, for example, adding water-miscible organic solvents such as ethanol and dimethyl sulfoxide, and a known buffering agent to purified water.

The block copolymer having a signal group of the present invention, or a composition including such block copolymer may be used as a molecular probe for molecular imaging. The signal group is as described above. Regarding the signal group, a single kind of signal group or a combination of a plurality of kinds thereof may be used. Such molecular probe for molecular imaging has high migration characteristics to a tissue such as a tumor or an inflammation site and high penetrability into the interior of a tissue, and enables performing of imaging at a tumor or an inflammation site. Furthermore, since the block copolymer or the composition also has excretability through the kidneys and the like, the block copolymer or the composition also has a feature that the in vivo retention characteristics exhibited by a polymeric DDS preparation are well controlled, and undesirable migration to normal tissues is suppressed.

In a case in which the block copolymer having a signal group of the present invention, or a composition including the block copolymer is used as a molecular probe for molecular imaging, the molecular probe may be used for any one of oral route of administration and parenteral route of administration. It is preferable that the molecular probe is prescribed based on a route of administration by parenteral injection. Administration by injection is carried out by intravenous administration, intraarterial administration, subcutaneous administration, intramuscular administration, intratumoral administration, or the like.

In a case in which the block copolymer of the present invention or a composition including the block copolymer includes a physiologically active substance as a hydrophobic substituent or a hydrophobic substance thereof, the block copolymer or the composition may be caused to have physical properties of slowly releasing the physiologically active substance after being administered into the living body. The physiologically active substance thus released may be caused to exhibit pharmacological effects. Consequently, a block copolymer including a physiologically active substance, or a composition including the block copolymer may also be used as a pharmaceutical product that includes the physiologically active substance as an active ingredient.

In a case in which the block copolymer including a physiologically active substance, and a composition including the block copolymer, is used as a pharmaceutical product, the pharmaceutical product may be used by any of oral and parenteral administration routes. It is preferable that the pharmaceutical products are prescribed via an administration route based on parenteral injection. Administration by injection is carried out by intravenous administration, intraarterial administration, subcutaneous administration, intramuscular administration, intratumoral administration, or the like.

In regard to the formulation of the block copolymer, and the composition including the block copolymer of the present invention, pharmacologically acceptable carriers that are conventionally used, for example, an excipient, an extending agent, a filler, a binding agent, a wetting agent, a disintegrant, a lubricating agent, a surfactant, a dispersant, a buffering agent, a preservative, a dissolution aid, an antiseptic agent, a flavoring agent, a soothing agent, a stabilizer, a solvent, a solvating agent, a suspending agent, a colorant, a fragrance, and an isotonizing agent may be used.

In the case of an injectable preparation, a solvent is usually used. Such solvent include water, physiological saline, a 5% glucose or mannitol solution, a water-soluble organic solvent such as, for example, glycerol, ethanol, dimethyl sulfoxide, N-methylpyrrolidone, polyethylene glycol, or chromophore, and mixed liquids thereof, as well as a mixed liquid of water and the water-soluble organic solvent. It is preferable to produce an administrable preparation using these additives for formulation, and to use the preparation.

The dosage amount of administration of the block copolymer of the present invention or a composition including the block copolymer may be naturally changed depending on the type of the signal group and/or physiologically active substance to be included, or the gender, age, physiological condition, or pathological condition of the patient, or the like. However, it is preferable that the block copolymer or the composition is usually administered parenterally in an amount of 0.01 to 500 mg/m$^2$, and preferably 0.1 to 250 mg/m$^2$, in terms of the active ingredient, per day for an adult.

EXAMPLES

Hereinafter, the present invention will be explained in more detail by way of Examples. However, the invention is not intended to be limited to these Examples.

Measurement of the average particle sizes of the block copolymers of Synthesis Examples and Examples and compositions including those block copolymers was carried out using a single nanoparticle size analyzer, IG-1000, manufactured by Shimadzu Corp. (measurement temperature: 25° C., light intensity at t=0: 100 to 200). Regarding the sample for measuring the average particle size, a solution produced using ultrapure water to a block copolymer concentration of 1 mg/mL or 2 mg/mL and filtered through a 0.45 μm membrane filter, was used.

In the Examples, Nile Red derivative refers to 2-(2-aminoethoxy)-9-(diethylamino)-5H-benzo[a]phenoxazin-5-one.

[Synthesis Example 1] Synthesis of Polyethylene Glycol-Polyglutamic Acid Block Copolymer (Polyethylene Glycol Molecular Weight: 2 kDa, Number of Units of Polyglutamic Acid: 7.9)

A polyethylene glycol having one terminal methoxy group and another terminal 3-aminopropyl group (SUNBRIGHT M89506, manufactured by NOF Corp., average molecular weight: 2 kDa, 14 g) was dissolved in DMSO (280 mL), subsequently γ-benzyl L-glutamic acid-N-carboxyanhydride (16.8 g) was added thereto, and the mixture was stirred for 22.5 hours at 30° C. The reaction liquid was added dropwise for 2.0 hours into a mixed liquid of diisopropyl ether (5,040 mL) and ethanol (560 mL), and the mixture was stirred for 4.0 hours at room temperature. Subsequently, the supernatant was removed, a mixed solution of diisopropyl ether (1,800 mL) and ethanol (200 mL) was added to the residue, and the mixture was stirred to obtain a precipitate. The precipitate was collected by filtration and dried under reduced pressure. Thereby, a polymerization product (31.9 g) was obtained.

The polymerization product (30.0 g) thus obtained was dissolved in DMF (336 mL), acetic anhydride (6.0 mL) was added thereto, and the mixture was stirred for 18 hours at 20° C. The reaction liquid was added dropwise for 2.5 hours into a mixed liquid of diisopropyl ether (3,024 mL) and ethyl acetate (336 mL), and the mixture was stirred for 6.0 hours at room temperature. Subsequently, the supernatant was removed, a mixed solution of diisopropyl ether (1,800 mL) and ethanol (200 mL) was added to the residue, and the mixture was stirred for 1.5 hours to obtain a precipitate. Subsequently, the precipitate was collected by filtration and dried under reduced pressure, and thereby, an acetylated polymer (23.7 g) was obtained.

The acetylated polymer (22.0 g) thus obtained was dissolved in DMF (515 mL), and 10% palladium-carbon (4.4 g) was added thereto. Subsequently, the reaction atmosphere was purged with hydrogen, and hydrogenolysis was performed for 65 hours at 30° C. and 1 atmosphere. The 10% palladium-carbon catalyst was separated by filtration (200 mL of ethyl acetate was used for washing down), subsequently the filtrate was added dropwise for 1.5 hours into a mixed liquid of heptanes (3,000 mL) and ethyl acetate (1,200 mL), and the mixture was stirred for 5.0 nights at room temperature. Subsequently, the supernatant was removed, a mixed liquid of heptane (1,333 mL) and ethyl acetate (667 mL) was added to the residue, and the mixture was stirred for 0.5 hours to obtain a precipitate. Subsequently, the precipitate was collected by filtration and dried under reduced pressure. This precipitate (15.0 g) was dissolved in 5% saline (1,500 mL), and the pH of the solution was adjusted to about 11 with a 2.2 N aqueous solution of sodium hydroxide. Subsequently, the solution was purified using partition/adsorption resin column chromatography (HP-20) and then using ion exchange resin column chromatography (Dowex 50). The solution thus eluted was concentrated under reduced pressure and then freeze-dried, and thereby a polyethylene glycol-polyglutamic acid block copolymer (Synthesis Example 1: 12.3 g) was obtained.

In regard to Synthesis Example 1, the number of units of glutamic acid was calculated to be 7.9, by a titration method using 0.1 N potassium hydroxide. From this, the average molecular weight of the main chain polymer combining a polyethylene glycol chain and a polyamino acid chain was calculated to be 3,062≈3 kDa from the sum of the molecular weight of the polyethylene glycol chain (2,000), the molecular weight of the glutamic acid 7.9 unit (129.11×7.9=1,020), and the terminal acetyl group of the polyamino acid (42).

[Synthesis Example 2] Synthesis of Polyethylene Glycol-α,β-Polyaspartic Acid Block Copolymer (Polyethylene Glycol Molecular Weight: 12 kDa, Number of Units of Polyaspartic Acid: 23.8)

A polyethylene glycol having one terminal methoxy group and another terminal 3-aminopropyl group (SUNBRIGHT MEPA-12K, manufactured by NOF Corp., average molecular weight: 12 kDa, 75.0 g) was dissolved in DMSO (1,430 mL), subsequently γ-benzyl L-aspartic acid-N-carboxyanhydride (45.0 g, 29 equivalents) was added to the solution, and the mixture was stirred overnight at 32.0° C. The reaction liquid was added dropwise for one hour into a mixed liquid of diisopropyl ether (12 L) and ethanol (3 L), and the mixture was stirred for one hour at room temperature to obtain a precipitate. Subsequently, the precipitate was collected by filtration and dried under reduced pressure, and thereby a polymerization product (106.0 g) was obtained.

The polymerization product (105.0 g) thus obtained was dissolved in DMF (1,050 mL), and acetic anhydride (3.3 mL) was added thereto, and the mixture was stirred for 3 hours at 35° C. The reaction liquid was added dropwise for one hour into a mixed liquid of diisopropyl ether (2,9450 mL) and ethanol (1,050 mL), and the mixture was stirred for one hour at room temperature to obtain a precipitate. Subsequently, the precipitate was collected by filtration and dried under reduced pressure, and thereby an acetylated polymer (103.0 g) was obtained.

The acetylated polymer (100.0 g) thus obtained was dissolved in acetonitrile (2 L), subsequently 0.2 Normal sodium hydroxide (2 L) was added to the solution, and hydrolysis was performed for 3 hours at 23° C. 2 Normal hydrochloric acid was added to the reaction liquid to neutralize the reaction liquid, and then acetonitrile was removed by concentration under reduced pressure. Subsequently, the liquid concentrate was washed three times using ethyl acetate (2 L). The aqueous layer was concentrated under reduced pressure, and then the pH of the solution was adjusted to 11.0 with a 1 Normal aqueous solution of sodium hydroxide. Table salt (100 g) was added thereto, and the mixture was purified using partition/adsorption resin column chromatography and then using ion exchange resin column chromatography. The solution thus eluted was concentrated under reduced pressure and then was freeze-dried. Thereby, a polyethylene glycol-polyaspartic acid block copolymer (Synthesis Example 2: 75.4 g) was obtained.

In regard to Synthesis Example 2, the number of units of aspartic acid was calculated to be 23.8 by a titration method using 0.1 N potassium hydroxide. From this, the average molecular weight of the main chain polymer combining a polyethylene glycol chain and a polyamino acid chain was calculated to be 14,781≈15 kDa from the sum of the molecular weight of the polyethylene glycol chain (12,000), the molecular weight of the aspartic acid 23.8 unit (115.09×23.8=2,739), and the terminal acetyl group of the polyamino acid (42).

[Synthesis Example 3] Synthesis of Polyethylene Glycol-α,β-Polyaspartic Acid Block Copolymer (Polyethylene Glycol Molecular Weight: 2 kDa, Number of Units of Polyaspartic Acid: 12.5)

A polyethylene glycol having one terminal methoxy group and another terminal 3-aminopropyl group (SUNBRIGHT MEPA-20H, manufactured by NOF Corp., average molecular weight: 2 kDa, 20.0 g) was dissolved in DMSO (400 mL), and then γ-benzyl L-aspartic acid-N-carboxyanhydride (29.8 g, 12 equivalents) was added to the solution. The mixture was stirred for 20 hours at 32.5° C. The reaction liquid was added dropwise for one hour into a mixed liquid of diisopropyl ether (3,200 mL) and ethanol (800 mL), and the mixture was stirred for 3 hours at room temperature to obtain a precipitate. Subsequently, the precipitate was collected by filtration and dried under reduced pressure, and thus a polymerization product (31.2 g) was obtained.

The polymerization product (30.0 g) thus obtained was dissolved in DMF (300 mL), and acetic anhydride (7.3 mL) was added thereto. The mixture was stirred for 3 hours at 35° C. The reaction liquid was added dropwise for one hour into a mixed liquid of diisopropyl ether (2,700 mL) and ethanol (300 mL), and the mixture was stirred for one hour at room temperature to obtain a precipitate. Subsequently, the precipitate was collected by filtration and dried under reduced pressure, and thereby an acetylated polymer (26.6 g) was obtained.

The acetylated polymer (25.0 g) thus obtained was dissolved in MeCN (500 mL), and then 0.2 Normal sodium hydroxide (500 mL) was added thereto. The mixture was subjected to hydrolysis for 3 hours at 23° C. 2 Normal hydrochloric acid was added to the reaction liquid to neutralize the reaction liquid, and then acetonitrile was removed by concentration under reduced pressure. Subsequently, the liquid concentrate was washed three times using ethyl acetate (500 mL). The aqueous layer was concentrated under reduced pressure, and then the pH of the solution was adjusted to 11.0 with a 1 Normal aqueous solution of sodium hydroxide. Table salt (50 g) was added thereto, and then the mixture was purified by partition/adsorption resin column chromatography and then using ion exchange resin column chromatography. The solution thus eluted was concentrated under reduced pressure and then freeze-dried, and a polyethylene glycol-polyaspartic acid block copolymer (Synthesis Example 3: 13.0 g) was obtained.

In regard to Synthesis Example 3, the number of units of aspartic acid was calculated to be 12.5 by a titration method using 0.1 N potassium hydroxide. From this, the average molecular weight of the main chain polymer combining a polyethylene glycol chain and a polyamino acid chain was calculated to be 3,481≈3 kDa.

[Example 1] Synthesis of 4-Phenyl-1-Butanol-Bonded and Nile Red Derivative-Bonded Product of Polyethylene Glycol (2 kDa)-Polyglutamic Acid (7.9 Polymerization Units) Block Copolymer The product of Synthesis Example 1 (1,000 mg), a Nile Red derivative (manufactured by Tokyo Chemical Industry Co., Ltd., 46.9 mg), and 4-dimethylaminopyridine (DMAP, 315 mg) were dissolved in DMF (21 mL), and diisopropylcarbodiimide (DIPCI, 38 μL) was added thereto. The mixture was stirred for 5 hours at 25° C. Subsequently, 4-phenyl-1-butanol (266 µL) and 794 µL were added to the mixture, and the resulting mixture was stirred for 15 hours. Subsequently, 397 µL of DIPCI was added thereto, and the mixture was stirred for 5.5 hours. The reaction liquid was transferred into a dialysis membrane having a MWCO of 1,000, and dialysis was performed using water as the external liquid. The internal liquid was freeze-dried, and thereby a product was obtained. The product thus obtained was dissolved in acetonitrile/water (50/50 (v/v), 50 mL), subsequently the solution was transferred into a dialysis membrane having a MWCO of 1,000, and dialysis was performed using acetonitrile/water (50/50 (v/v)) as the external liquid. Subsequently, dialysis was performed using acetonitrile as the external liquid. After completion of the dialysis, water was added to the internal liquid so that the internal liquid becomes acetonitrile/water (50/50 (v/v)). An ion exchange resin (DOWEX 50) was added thereto, and the mixture was stirred for 0.5 hours at room temperature. The ion exchange resin was separated by filtration, and then acetonitrile was distilled off under reduced pressure. The residue was freeze-dried, and thereby, the titled 4-phenyl -1-butanol-bonded block copolymer (Example 1: 1,012 mg) was obtained.

The product of Example 1 was subjected to a hydrolysis treatment using a 1 N aqueous solution of sodium hydroxide, and 4-phenyl-1-butanol thus released was quantitatively determined by high performance liquid chromatography (HPLC). Thus, the content of 4-phenyl-1-butanol was determined. As a result, the content of 4-phenyl-1-butanol in Example 1 was 15.9% by mass. The amount of bonding of Nile Red derivative was 0.37 molecules as determined from the consumption ratio of the Nile Red derivative in the reaction solution analyzed by HPLC. Consequently, the total molecular weight of the Nile Red derivative of Example 1 was calculated to be 138≈0.1 kDa.

From these values, the total molecular weight of Example 1 was calculated to be 4,169≈4 kDa. Furthermore, the average molecular weight of the main chain polymer combining the polyethylene glycol chain and the polyamino acid chain was calculated to be 3,062≈3 kDa.

From this, the content of the Nile Red derivative in Example 1 was 3.32% by mass, the content of 4-phenyl-1-butanol was 15.9% by mass, and the content of the polyethylene glycol segment was 48.0% by mass.

The particle size was measured using IG-1000, and the average particle size was 18 nm (2 mg/mL).

[Example 2] Synthesis of Cabazitaxel (CBZ)-Bonded, n-Butylamine-Bonded, and Nile Red Derivative-Bonded Product of Polyethylene Glycol (2 kDa)-α,β-Polyaspartic Acid (12.5 Polymerization Units) Block Copolymer The product of Synthesis Example 3 (205.6 mg), cabazitaxel (CBZ, 166.3 mg), and a Nile Red derivative (5.1 mg) were dissolved in NMP (5.7 mL), and n-butylamine (36 µL), DMAP (45.0 mg), and DIPCI (265 µL) were added to the solution. The mixture was stirred for 17.5 hours at 20° C. Subsequently, DIPCI (66 µL) was further added thereto, and the mixture was stirred for another 4.5 hours. Ethyl acetate (5.5 mL) was added to the reaction liquid, and then the mixture was added dropwise for 10 minutes into diisopropyl ether (440 mL). The mixture was stirred for one hour at room temperature to obtain a precipitate, and then the precipitate was collected by filtration and dried under reduced pressure. Thus, a product (300 mg) was obtained. The product thus obtained was dissolved in acetonitrile/water (50/50 (v/v), 20 mL), and then an ion exchange resin was added to the solution. The mixture was stirred for 30 minutes at 5° C. The ion exchange resin was separated by filtration, and then acetonitrile was distilled off under reduced pressure and freeze-dried. Thereby, the titled taxane-bonded polymer derivative (Example 2: 270.9 mg) was obtained.

The amount of CBZ bonded to Example 2 was 1.7 molecules as determined from the consumption ratio of CBZ in the reaction solution measured by HPLC. Consequently, the total CBZ molecular weight of Example 2 was calculated to be 1,421≈1 kDa.

The amount of n-butylamine bonded to Example 2 was 6.2 molecules under the assumption that the entire input amount of n-butylamine had reacted. Consequently, the total molecular weight of n-butylamine of Example 2 was calculated to be 453≈0.4 kDa.

The amount of the Nile Red derivative bonded to Example 2 was 0.23 molecules as determined from the consumption ratio of the Nile Red derivative in the reaction solution measured by HPLC. Consequently, the total molecular weight of the Nile Red derivative NR of Example 2 was calculated to be 87≈0.1 kDa.

From these values, the total molecular weight of Example 2 was calculated to be 5,846≈6 kDa. Furthermore, the average molecular weight of the main chain polymer combining the polyethylene glycol chain and the polyamino acid chain was calculated to be 3,481≈3 kDa.

From this the content of CBZ in Example 2 was 24.3% by mass, the content of n-butylamine was 7.8% by mass, the content of the Nile Red derivative was 1.5% by mass, and the content of the polyethylene glycol segment was 34.2% by mass.

The particle size was measured using IG-1000, and the average particle size was 14 nm (1 mg/mL).

Example 3

Synthesis of 7-ethyl-10-hydroxycamptothecin (EHC)-Bonded and ALEXA FLUOR (registered trademark) 594 Cadaverin (Alexa)-Bonded Product of Polyethylene Glycol (2 kDa)-Polyglutamic Acid (8.3 Polymerization Units) Block Copolymer A polyethylene glycol (2 kilodaltons)-polyglutamic acid (8.3 polymerization units) block copolymer (40.0 mg) synthesized by a method similar to that of Synthesis Example 1, ALEXA FLUOR (registered trademark) 594 cadaverin (Alexa, manufactured by Life Technologies Corp., 2.00 mg), and 7-ethyl-10-hydroxycamptothecin (EHC, manufactured by ScinoPharm Taiwan, Ltd., 20.0 mg) were dissolved in DMF (3.20 mL), and the solution was stirred for 20 minutes at 35° C. Subsequently, 4-dimethylaminopyridine (DMAP, 1.98 mg) was added thereto, and the mixture was stirred for 45 minutes at 25° C. Subsequently, diisopropylcarbodiimide (DIPCI, 33.1 µL) was added thereto, and the mixture was stirred for 21 hours at 25° C. The reaction liquid was added dropwise into a mixed liquid of diisopropyl ether (43.2 mL) and ethyl acetate (4.8 mL), and the mixture was stirred at room temperature. Subsequently, 38.0 mL of the supernatant was removed, and a mixed liquid of diisopropyl ether (21.6 mL) and ethyl acetate (2.4 mL) was added to the residue. Subsequently, the mixture was stirred at room temperature to obtain a precipitate, and the precipitate was collected by filtration and dried under reduced pressure, and thereby a product was obtained (49.7 mg). The product thus obtained was dissolved in acetonitrile/water (98.7/1.3 (v/v), 1.5 mL), subsequently an ion exchange resin (DOWEX 50) was added thereto, and the mixture was stirred for 30 minutes at 0° C. The ion exchange resin was separated by filtration, subsequently acetonitrile was distilled off under reduced pressure, and the residue was freeze-dried. Thereby, the titled 7-ethyl-10-hydroxycamptothecin-bonded and ALEXA FLUOR (registered trademark) 594 cadaverin-bonded product of a polyethylene glycol (2 kilodaltons)-polyglutamic acid (8.3 polymerization units) block copolymer (Example 3: 48.8 mg) was obtained.

The amount of EHC bonded to Example 3 was 3.9 molecules as determined from the consumption ratio of EHC in the reaction solution measured by high performance liquid chromatography (HPLC). Consequently, the total molecular weight of EHC of Example 3 was calculated to be 1,530≈2 kDa.

The amount of Alexa bonded to Example 3 was 0.19 molecules as determined from the consumption ratio of Alexa in the reaction solution measured by high performance liquid chromatography (HPLC). Consequently, the molecular weight of Alexa of Example 3 was calculated to be 153≈0.2 kDa.

From these values, the total molecular weight of Example 3 was calculated to be 4,690≈5 kDa. Furthermore, the average molecular weight of the main chain polymer combining a polyethylene glycol chain and a polyamino acid chain was calculated to be 3,114≈3 kDa.

From this the content of EHC in Example 3 was 32.5% by mass, the content of Alexa was 3.29% by mass, and the content of the polyethylene glycol segment was 42.6% by mass.

The particle size was measured using IG-1000, and the average particle size was 10 nm (1 mg/mL).

[Comparative Example 1] Synthesis of 4-phenyl-1-Butanol-Bonded and Nile Red Derivative-Bonded Product of Polyethylene Glycol (12 kDa)-Polyglutamic Acid (22.0 Polymerization Units) Block Copolymer A polyethylene glycol (12 kDa)-polyglutamic acid (22.0 polymerization units) block copolymer (676 mg) synthesized by a method similar to that of Synthesis Example 1, a Nile Red derivative (manufactured by Tokyo Chemical Industry Co., Ltd., 17.0 mg) and DMAP (122 mg) were dissolved in DMF (8.0 mL), and DIPCI (14 μL) was added to the solution. The solution was stirred for 1.5 hours at 25° C. Subsequently, 4-phenyl-1-butanol (102 mg) and DIPCI (308 μL) was added thereto, and the mixture was stirred for 25 hours. Subsequently, the reaction liquid was added dropwise into a mixed liquid of diisopropyl ether (120 mL), ethanol (15 mL), and ethyl acetate (15 mL), and the mixture was stirred at room temperature to obtain a precipitate. Subsequently, the precipitate was collected by filtration and dried under reduced pressure, and thus a product was obtained (770 mg). The product thus obtained was dissolved in acetonitrile/water (50/50 (v/v), 20 mL), and then an ion exchange resin (DOWEX 50) was added to the solution. The mixture was stirred for 2.0 hours at 0° C. The ion exchange resin was separated by filtration, and then acetonitrile was distilled off under reduced pressure. The residue was freeze-dried, and thereby, the title 4-phenyl-1-butanol-bonded and Nile Red derivative-bonded product of a polyethylene glycol (12 kDa)-polyglutamic acid (22.0 polymerization units) block copolymer (Comparative Example 1: 720 mg) was obtained.

The amount of 4-phenyl-1-butanol bonded to Comparative Example 1 was 15 molecules as determined from the consumption ratio of 4-phenyl-1-butanol in the reaction solution measured by HPLC. Consequently, the total molecular weight of 4-phenyl-1-butanol of Comparative Example 1 was calculated to be 2,224≈2 kDa.

The amount of the Nile Red derivative bonded to Comparative Example 1 was 1 molecule as determined from the consumption ratio of the Nile Red derivative in the reaction solution measured by HPLC. Consequently, the total molecular weight of the Nile Red derivative in Comparative Example 1 was calculated to be 376≈0.4 kDa.

From these values, the total molecular weight of Comparative Example 1 was 18,091≈18 kDa, and the average molecular weight of the main chain polymer combining the polyethylene glycol chain and the polyamino acid chain was calculated to be 14,882≈15 kDa.

From this, the content of 4-phenyl-1-butanol in Comparative Example 1 was 12% by mass, the content of the Nile Red derivative was 2.1% by mass, and the content of the polyethylene glycol segment was 67% by mass.

The particle size was measured using IG-1000, and the average particle size was 36 nm (2 mg/mL).

[Comparative Example 2] Synthesis of Cabazitaxel (CBZ)-Bonded and Nile Red Derivative-Bonded Product of Polyethylene Glycol (12 kDa)-α,β-Polyaspartic Acid (23.8 Polymerization Units) Block Copolymer The product of Synthesis Example 2 (200 mg), cabazitaxel (CBZ, 99.7 mg), and a Nile Red derivative (5.2 mg) were dissolved in N-methylpyrrolidone (NMP, 2.5 mL), and DMAP (4.4 mg) and DIPCI (118 μL) were added to the solution. The mixture was stirred for 21 hours at 20° C. Subsequently, DIPCI (29 μL) was further added thereto, and the mixture was further stirred for another 5 hours. The reaction liquid was added dropwise for 10 minutes into a mixed liquid of diisopropyl ether (18 mL) and ethanol (4.5 mL), and the mixture was stirred for one hour at room temperature to obtain a precipitate. Subsequently, the precipitate was collected by filtration and dried under reduced pressure, and thereby a product (235.0 mg) was obtained. The product thus obtained was dissolved in acetonitrile/water (50/50 (v/v), 10 mL), and then an ion exchange resin was added to the solution. The mixture was stirred for 30 minutes at 5° C. The ion exchange resin was separated by filtration, and then acetonitrile was distilled off under reduced pressure. The residue was freeze-dried, and thereby, the titled taxane-bonded polymer derivative (Comparative Example 2: 205.6 mg) was obtained.

The amount of CBZ bonded to Comparative Example 2 was 4.3 molecules as determined from the consumption ratio of CBZ in the reaction solution measured by HPLC. Consequently, the total CBZ molecular weight of Comparative Example C-2 was calculated to be 3,594≈4 kDa.

The amount of the Nile Red derivative bonded to Comparative Example 2 was 1.0 molecule as determined from the consumption ratio of the Nile Red derivative in the reaction solution measured by HPLC. Consequently, the total molecular weight of the Nile Red derivative of Comparative Example 2 was calculated to be 377≈0.4 kDa.

From these values, the total molecular weight of Comparative Example 2 was calculated to be 20,988≈21 kDa. Furthermore, the average molecular weight of the main chain polymer combining a polyethylene glycol chain and a polyamino acid chain was calculated to be 14,781≈15 kDa.

From this, the content of CBZ in Comparative Example 2 was 17.1% by mass, the content of the Nile Red derivative was 1.8% by mass, and the content of the polyethylene glycol segment was 57.2% by mass.

The particle size was measured using IG-1000, and the average particle size was 29 nm (1 mg/mL).

[Comparative Example 3] Synthesis of Nile Red Derivative-Bonded Product of Polyethylene Glycol (2 kDa)-α,β-Polyaspartic Acid (12.5 Polymerization Units) Block Copolymer The product of Synthesis Example 3 (205.7 mg) and a Nile Red derivative (5.1 mg) were dissolved in N-methylpyrrolidone (NMP, 5.7 mL), and DMAP (45.0 mg) and DIPCI (265 µL) were added to the solution. The mixture was stirred for 18.5 hours at 20° C. Subsequently, DIPCI (66 µL) was further added thereto, and the mixture was stirred for another 2.5 hours. The reaction liquid was transferred into a dialysis membrane having a MWCO of 10,000, and dialysis was performed in water. Subsequently, the internal liquid was freeze-dried, and thereby the titled taxane-bonded polymer derivative (Comparative Example 3: 247.7 mg) was obtained.

The amount of the Nile Red derivative bonded to Comparative Example 3 was 0.3 molecules as determined from the consumption ratio of the Nile Red derivative in the reaction solution measured by HPLC. Consequently, the total molecular weight of the Nile Red derivative of Comparative Example 3 was calculated to be 113≈0.1 kDa.

From these values, the total molecular weight of Comparative Example 3 was calculated to be 5,126≈5 kDa. The average molecular weight of the main chain polymer combining a polyethylene glycol chain and a polyamino acid chain was calculated to be 3,481≈3 kDa.

From this, the content of the Nile Red derivative in Comparative Example 3 was 2.2% by mass, and the content of the polyethylene glycol segment was 39.0% by mass.

Comparative Example 3 was used as a fluorescent marked body of Synthesis Example 3 in the distribution test that will be described below.

[Test Example 1] Intratumoral and Intrarenal Distribution Test

Tumor masses of human pancreatic cancer BxPC-3 that had been subcultured by subcutaneous transplantation in BALB/c nude mice were cut into blocks having a size of about 3 mm on each side. The tumor blocks were subcutaneously transplanted into the dorsal side of nude mice using an injection needle-attached syringe. The product of Comparative Example 1 and Example 1 were respectively dissolved in a 5% glucose injection solution, and the solutions were respectively administered once intravenously in an amount of 5 mg/kg in terms of the Nile Red derivative. One hour after the administration, the mice were exsanguinated under isoflurane anesthesia, frozen embedded sections of extracted tumor and kidney were produced, and fluorescence was observed. The results are presented in FIG. 1.

Figure 2:
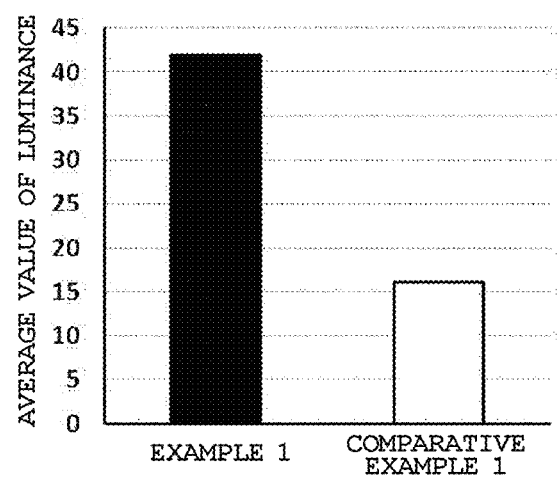
FIG. 2 is a graph for calculating luminances of the tumor tissue section images of Test Example 1.
Figure 3:
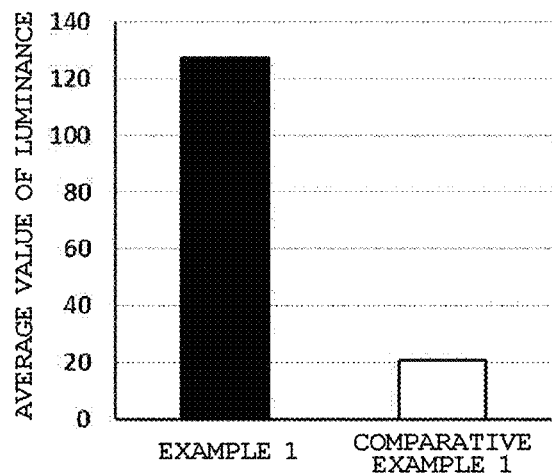
FIG. 3 is a graph for calculating the luminances of the kidney tissue section images of Test Example 1.

Furthermore, luminances were calculated based on those images using IMAGE-PRO PREMIER (Media Cybernetics). The luminance values in the tumors are presented in FIG. 2, and the luminance values in the kidneys are presented in FIG. 3.

As the results of Test Example 1, Example 1 penetrated into the entire tumor, and fluorescence signals were observed in a wider area, compared to Comparative Example 1. In the kidney, fluorescence was observed in the blood vessels and renal tubules in the case of Example 1, while fluorescence was not recognized in areas other than in the blood vessels in the case of Comparative Example 1. From the above results, it was found that Example 1 is capable of penetrating into the deep part of a tumor tissue and has a property of possibly being subjected to rapid renal excretion, compared to Comparative Example 1.

[Test Example 2] Intratumoral and Intrarenal Distribution Test

Figure 4:
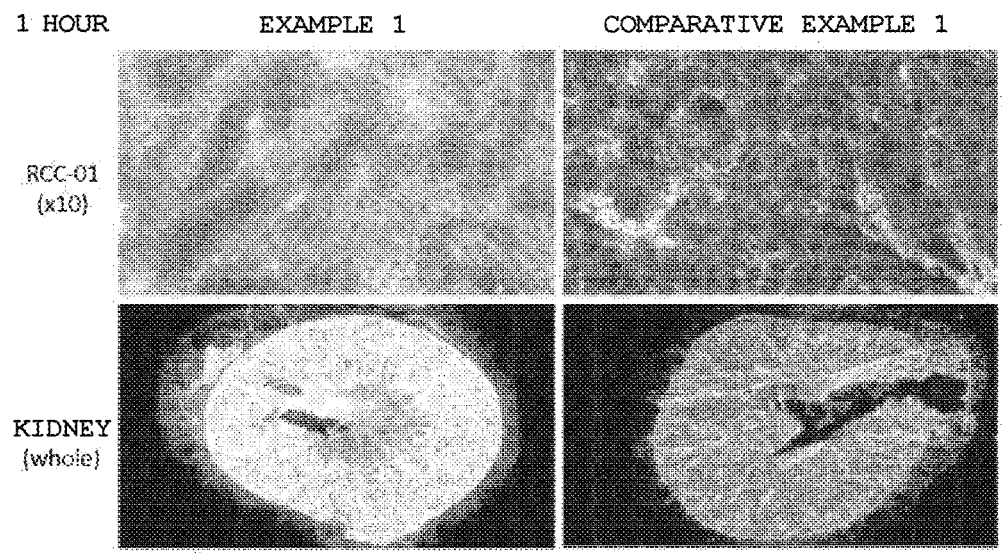
FIG. 4 is a set of tissue section images showing the distributions of the block copolymer of the present invention in a human renal cancer RCC-01-JCK tumor and in the kidney (Test Example 2).

Tumor masses of human renal cancer RCC-01-JCK that had been subcultured by subcutaneous transplantation in BALB/c nude mice were cut into blocks having a size of about 3 mm on each side. The tumor blocks were subcutaneously transplanted into the dorsal side of nude mice using an injection needle-attached syringe. The product of Comparative Example 1 and Example 1 were respectively dissolved in a 5% glucose injection solution, and the solutions were respectively administered once intravenously in an amount of 5 mg/kg in terms of the Nile Red derivative. One hour after the administration, the mice were exsanguinated under isoflurane anesthesia, frozen embedded sections of extracted tumor and kidney were produced, and fluorescence was observed. The results are presented in FIG. 4.

Figure 5:
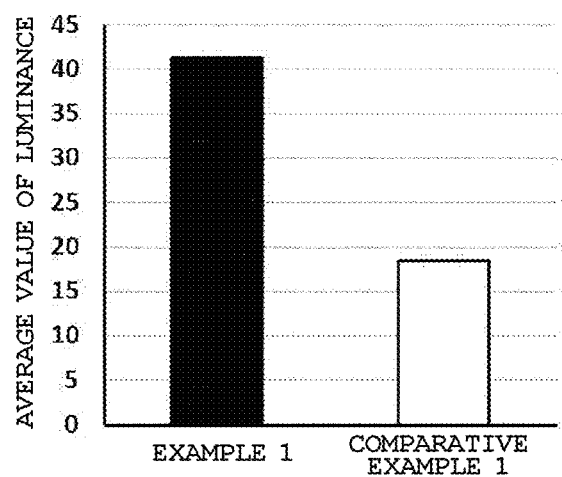
FIG. 5 is a graph for calculating the luminances of the tumor tissue section images of Test Example 2.
Figure 6:
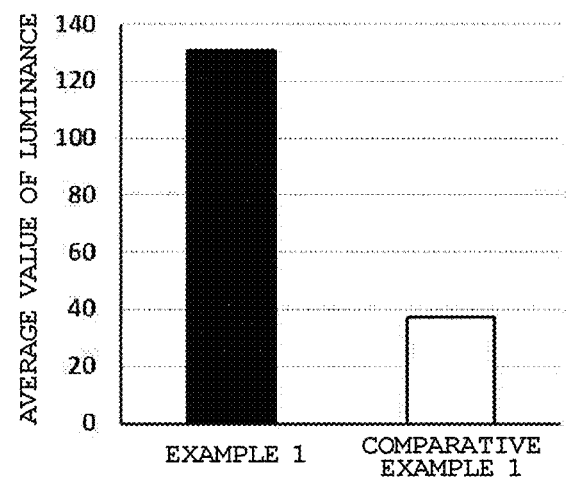
FIG. 6 is a graph for calculating the luminances of the kidney tissue section images of Test Example 2.

Furthermore, luminances were calculated based on those images using IMAGE-PRO PREMIER (Media Cybernetics). The luminance values in the tumors are presented in FIG. 5, and the luminance values in the kidneys are presented in FIG. 6.

As the results of Test Example 2, Example 1 penetrated into the entire tumor, and fluorescence signals were observed in a wider area, compared to Comparative Example 1. In the kidney, fluorescence was observed in the blood vessels and renal tubules in the case of Example 1, while fluorescence was not recognized in areas other than in the blood vessels in the case of Comparative Example 1. From the above results, it was found that Example 1 is capable of penetrating into the deep part of a tumor tissue and has a property of possibly being subjected to rapid renal excretion, compared to Comparative Example 1.

[Test Example 3] Intratumoral and Intrarenal Distribution Test

Figure 7:
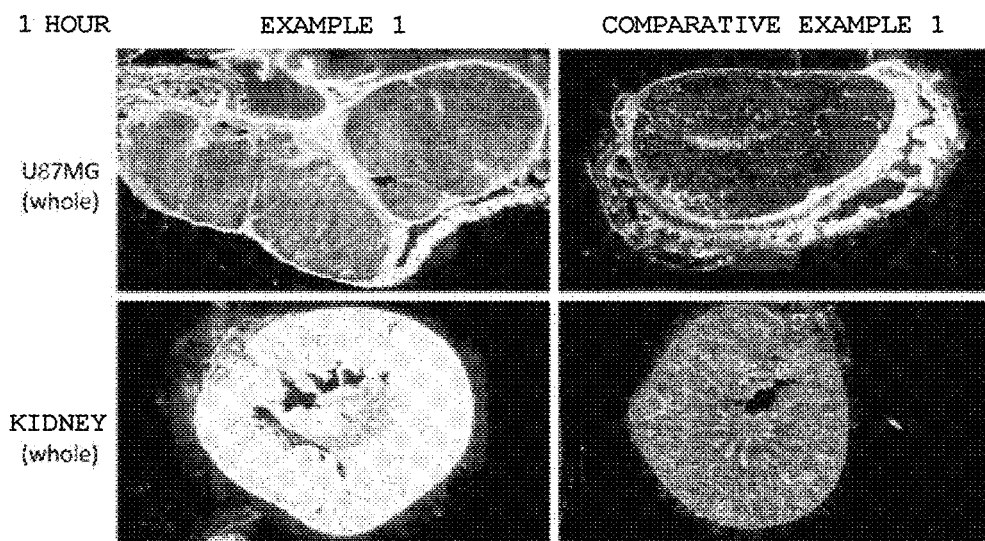
FIG. 7 is a set of tissue section images showing the distributions of the block copolymer of the present invention in a human glioma U87MG tumor and in the kidney (Test Example 3).

Tumor masses of human glioma U87MG that had been subcultured by subcutaneous transplantation in BALB/c nude mice were cut into blocks having a size of about 3 mm on each side. The tumor blocks were subcutaneously transplanted into the dorsal side of nude mice using an injection needle-attached syringe. The product of Comparative Example 1 and Example 1 were respectively dissolved in a 5% glucose injection solution, and the solutions were respectively administered once intravenously in an amount of 5 mg/kg in terms of the Nile Red derivative. One hour after the administration, the mice were exsanguinated under isoflurane anesthesia, frozen embedded sections of extracted tumor and kidney were produced, and fluorescence was observed. The results are presented in FIG. 7.

Figure 8:
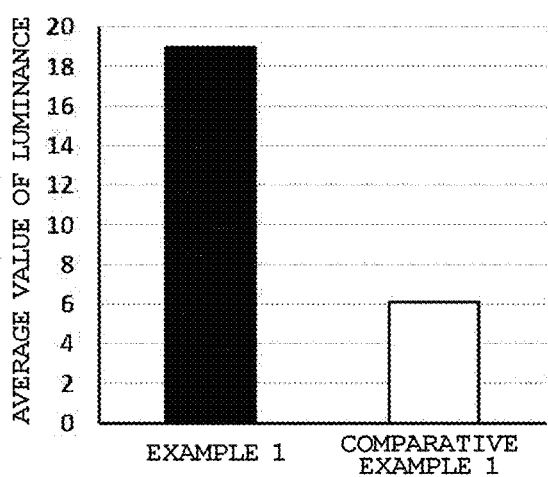
FIG. 8 is a graph for calculating the luminances of the tumor tissue section images of Test Example 3.
Figure 9:
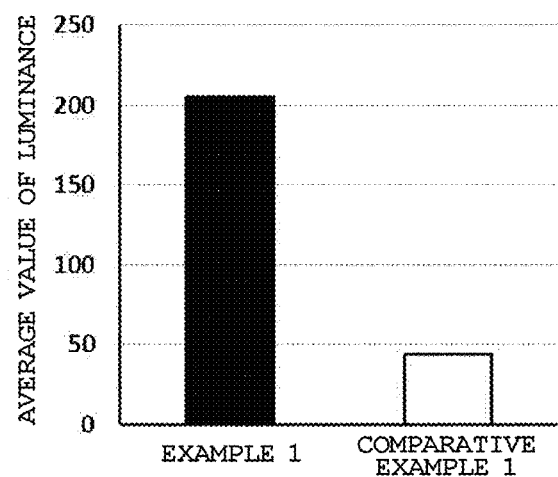
FIG. 9 is a graph for calculating the luminances of the kidney tissue section images of Test Example 3.

Furthermore, luminances were calculated based on those images using IMAGE-PRO PREMIER (Media Cybernetics). The luminance values in the tumors are presented in FIG. 8, and the luminance values in the kidneys are presented in FIG. 9.

As the results of Test Example 3, Example 1 penetrated into the entire tumor, and fluorescence signals were observed in a wider area, compared to Comparative Example 1. In the kidney, fluorescence was observed in the blood vessels and renal tubules in the case of Example 1, while fluorescence was not recognized in areas other than in the blood vessels in the case of Comparative Example 1. From the above results, it was found that Example 1 is capable of penetrating into the deep part of a tumor tissue and has a property of possibly being subjected to rapid renal excretion, compared to Comparative Example 1.

[Test Example 4] Intratumoral and Intrarenal Distribution Test

Figure 10:
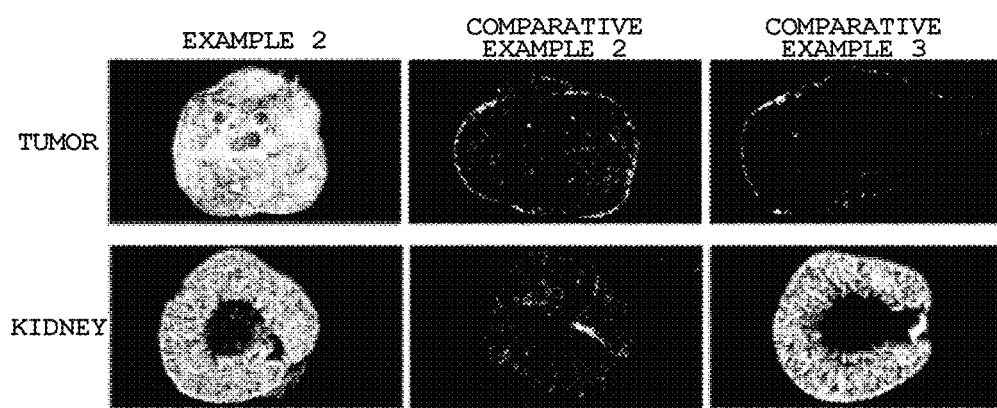
FIG. 10 is a set of tissue section images showing the distributions of the block copolymer of the present invention in a human pancreatic cancer BxPC3 tumor and in the kidney (Test Example 4).

Tumor masses of human pancreatic cancer BxPC3 that had been subcultured by subcutaneous transplantation in BALB/c nude mice were cut into blocks having a size of about 3 mm on each side. The tumor blocks were subcutaneously transplanted into the dorsal side of nude mice using an injection needle-attached syringe. The product of Example 2, Comparative Example 2, and Comparative Example 3 were respectively dissolved in a 5% glucose injection solution, and the solutions were respectively administered once intravenously in an amount of 5 mg/kg in terms of the Nile Red derivative. One hour after the administration, the mice were exsanguinated under isoflurane anesthesia, frozen embedded sections of extracted tumor and kidney were produced, and fluorescence was observed. The results are presented in FIG. 10.

As the results of Test Example 4, in the case of Example 2, signals of fluorescence were observed in a wide area of tumor sections. From this, it was found that the block copolymer of Example 2 may migrate and accumulate in a tumor tissue, and is capable of penetrating into the deep part of a tumor tissue. In contrast, in the case of Comparative Examples 2 and 3, fluorescence signals were observed in the outer periphery of tumors; however, tumor tissue penetrability was not confirmed, and the results showed poor migration characteristics and accumulation characteristics in a tumor tissue.

Furthermore, in the kidney, fluorescence was observed in the renal tubules in the case of Example 2 and Comparative Example 3. Meanwhile, in the case of Comparative Example 2, fluorescence was not recognized in areas other than in the blood vessels. From this, it was found that Example 2 has a property of possibly being subjected to rapid renal excretion, compared to Comparative Example 2.

The block copolymer of Comparative Example 3, in which the average molecular weight of the main chain polymer combining a polyethylene glycol chain and a polyamino acid chain was 3,481≈3 kDa, the mass content percentage of the signal group was 2.2%, and the mass content percentage of the hydrophobic substituent was 0%, was subject to rapid renal excretion; however, such block copolymer exhibited low accumulation properties in tumor. Furthermore, the block copolymer of Comparative Example 2 in which the average molecular weight of the main chain polymer combining a polyethylene glycol chain and a polyamino acid chain was 14,781≈15 kDa, was not subject to renal excretion; however, such block copolymer exhibited lower accumulation properties in tumor compared to Example 2.

It became clear that Example 2 in which the average molecular weight of the main chain polymer combining a polyethylene glycol chain and a polyamino acid chain was 3,481≈3 kDa, the mass content percentage of the signal group was 1.5%, and the mass content percentage of the hydrophobic substituent was 32%, was subject to rapid renal excretion and exhibited rapid tumor accumulation properties.

The invention claimed is:

1. An imaging probe comprising a block copolymer comprising a hydrophilic polymer segment linked to a hydrophobic polymer segment, the hydrophilic polymer segment containing a polyethylene glycol chain, and the hydrophobic polymer segment containing a polyamino acid chain having a signal group and optionally a hydrophobic substituent in a side chain, and wherein the block copolymer is represented by General Formula (1):

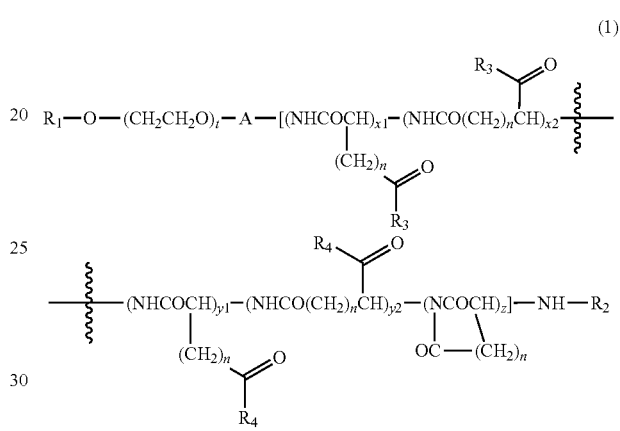

wherein $R_1$ represents a hydrogen atom or a linear, branched or cyclic (C1-C6) alkyl group which may have a substituent; t represents an integer from 20 to 140; A represents a (C1-C6) alkylene group which may have a substituent; $R_2$ represents a substituent selected from the group consisting of a hydrogen atom, a (C1-C6) acyl group, and a (C1-C6) alkoxycarbonyl group; $R_3$ represents a signal group; $R_4$ represents a hydrophobic substituent; n represents 1 or 2; $x_1$, $x_2$, $y_1$, $y_2$, and z each independently represents an integer from 0 to 20; $(x_1+x_2)$ represents an integer from 1 to 10; $(x_1+x_2+y_1+y_2+z)$ represents an integer from 3 to 20; and the various constituent units to which $R_3$ and $R_4$ are bonded, and a constituent unit formed by intramolecular cyclization of a side-chain carbonyl group constitute a structure with those constituent units being each independently randomly arranged;

wherein said signal group of R3 contains a fluorescent group, a radioisotope-containing group, or a magnetic group, said fluorescent group including a group derived from a member selected from the group consisting of a fluorescein-based dye, an indocyanine-based dye, a rhodamine-based dye, a BODIPY-based dye, a xanthene-based dye, a Nile Red-based dye and a quantum dot, said radioisotope-containing group including a group derived from a member selected from the group consisting of a sugar, an amino acid and a nucleic acid, all being labeled with radioisotopes, said magnetic group including a group selected from the group consisting of ferrichrome, ferrite nanoparticles and magnetic nanoparticles;

wherein the main chain polymer of the block copolymer combining the polyethylene glycol chain and the polyamino acid chain has an average molecular weight of not less than 2 kDa and not more than 10 kDa, said average molecular weight of the main chain polymer being a calculated value obtained by summing the (1) average molecular weight of the polyethylene glycol chain and the (2) average molecular weight of the polymer main chain portion of the polyamino acid chain excluding the signal group and the optional hydrophobic substituent, said average molecular weight of the polyethylene glycol chain being determined from the peak top molecular weight measured by a GPC method based on polyethylene glycol standards, and average molecular weight of the polymer main chain portion of the polyamino acid chain being a calculated value obtained by multiplying the average molecular weight of the polymerized monomer unit of the polyamino acid chain by the average number of units of the polyamino acid obtained by neutralization titration method, and a mass content percentage of the signal group and the optional hydrophobic substituent is not less than 5% by mass and not more than 50% by mass, and wherein the block copolymer has a particle size of less than 20 nm.

2. The imaging probe according to claim 1, wherein the signal group is a fluorescent group.

3. The imaging probe according to claim 1, wherein the polyethylene glycol chain has an average molecular weight of not less than 1 kDa and not more than 6 kDa.

* * * * *